(12) United States Patent
Beckett et al.

(10) Patent No.: US 12,357,352 B2
(45) Date of Patent: Jul. 15, 2025

(54) ADJUSTABLE DEVICES FOR TREATING ARTHRITIS OF THE KNEE

(71) Applicant: NuVasive Specialized Orthopedics, Inc., San Diego, CA (US)

(72) Inventors: Adam G. Beckett, San Diego, CA (US); Thomas B. Buford, San Diego, CA (US); Youngsam Bae, San Diego, CA (US); Edward H. Kim, San Diego, CA (US); Matthew Tobias Jacobs, San Diego, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 232 days.

(21) Appl. No.: 18/163,594

(22) Filed: Feb. 2, 2023

(65) Prior Publication Data

US 2023/0190340 A1    Jun. 22, 2023

Related U.S. Application Data

(63) Continuation of application No. 16/812,114, filed on Mar. 6, 2020, now Pat. No. 11,596,456, which is a
(Continued)

(51) Int. Cl.
*A61B 17/72* (2006.01)
*A61B 17/86* (2006.01)
(Continued)

(52) U.S. Cl.
CPC .......... *A61B 17/72* (2013.01); *A61B 17/7216* (2013.01); *A61B 17/7233* (2013.01);
(Continued)

(58) Field of Classification Search
CPC . A61B 17/72; A61B 17/7216; A61B 17/7233; A61B 17/8605; A61B 17/8095; A61B 2017/00199; A61B 2017/00398; A61B 2017/00402; A61B 2017/00411; A61B 2017/00477; A61B 2017/00539;
(Continued)

(56) References Cited

U.S. PATENT DOCUMENTS 5,356,411 A * 10/1994 Spievack ........... A61B 17/8004
606/63
9,848,914 B2 * 12/2017 Pool ................... A61B 17/7016
(Continued)

*Primary Examiner* — Eduardo C Robert
*Assistant Examiner* — David C Comstock

(57) ABSTRACT

Systems and related methods for changing the angle of a bone of a subject, the system may include a non-invasively adjustable implant configured to be placed inside a cavity within the bone. The non-invasively adjustable implant may couple to a first portion of bone and a second portion of bone that is separated or separable from the first portion of bone, such that non-invasive elongation of the adjustable implant causes movement of the first portion of bone and the second portion of bone apart angularly. The system may include an anchor configured to couple the non-invasively adjustable implant to bone. The non-invasively adjustable implant may include an anchor hole configured to receive the anchor therein.

18 Claims, 27 Drawing Sheets

Related U.S. Application Data continuation of application No. 15/953,453, filed on Apr. 15, 2018, now Pat. No. 10,617,453, which is a continuation of application No. PCT/US2016/057371, filed on Oct. 17, 2016.

(60) Provisional application No. 62/242,931, filed on Oct. 16, 2015.

(51) Int. Cl.
*A61B 17/00* (2006.01)
*A61B 17/68* (2006.01)
*A61B 17/80* (2006.01)

(52) U.S. Cl.
CPC .............. *A61B 17/8605* (2013.01); *A61B 2017/00199* (2013.01); *A61B 2017/00398* (2013.01); *A61B 2017/00402* (2013.01); *A61B 2017/00411* (2013.01); *A61B 2017/00477* (2013.01); *A61B 2017/00539* (2013.01); *A61B 2017/00867* (2013.01); *A61B 2017/00876* (2013.01); *A61B 2017/00991* (2013.01); *A61B 2017/681* (2013.01); *A61B 17/8095* (2013.01)

(58) Field of Classification Search
CPC ........... A61B 2017/00867; A61B 2017/00876; A61B 2017/00991
USPC ..................................................... 606/63, 64
See application file for complete search history.

(56) References Cited

U.S. PATENT DOCUMENTS

| | | | |
|---|---|---|---|
| 10,617,453 B2 | 4/2020 | Beckett et al. | |
| 2007/0233100 A1* | 10/2007 | Metzinger | A61B 17/748 606/62 |
| 2012/0209269 A1 | 8/2012 | Pool et al. | |
| 2014/0114311 A1* | 4/2014 | Pool | A61B 17/8872 606/62 |
| 2014/0250674 A1 | 9/2014 | Pool et al. | |
| 2014/0276828 A1* | 9/2014 | Howling | A61B 17/7233 606/64 |
| 2014/0330274 A1* | 11/2014 | Matityahu | A61B 17/748 606/304 |
| 2015/0057663 A1 | 2/2015 | Kinmon | |
| 2015/0057754 A1* | 2/2015 | Reed | A61F 2/4611 623/17.16 |
| 2015/0223854 A1* | 8/2015 | Skinlo | A61B 17/8095 606/70 |
| 2015/0313745 A1* | 11/2015 | Cheng | A61B 17/7216 602/19 |
| 2017/0100173 A1 | 4/2017 | Abdelgawad et al. | |
| 2017/0172624 A1* | 6/2017 | Brunner | A61B 17/7016 |
| 2020/0205866 A1 | 7/2020 | Beckett et al. | |

* cited by examiner

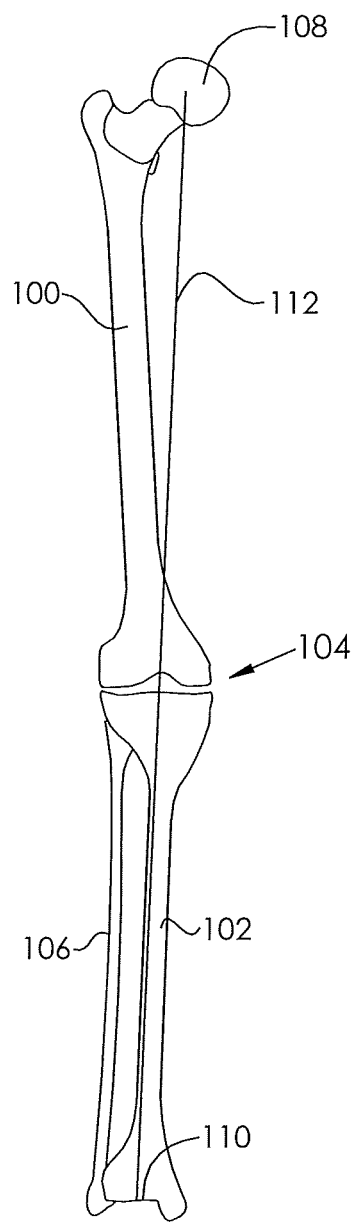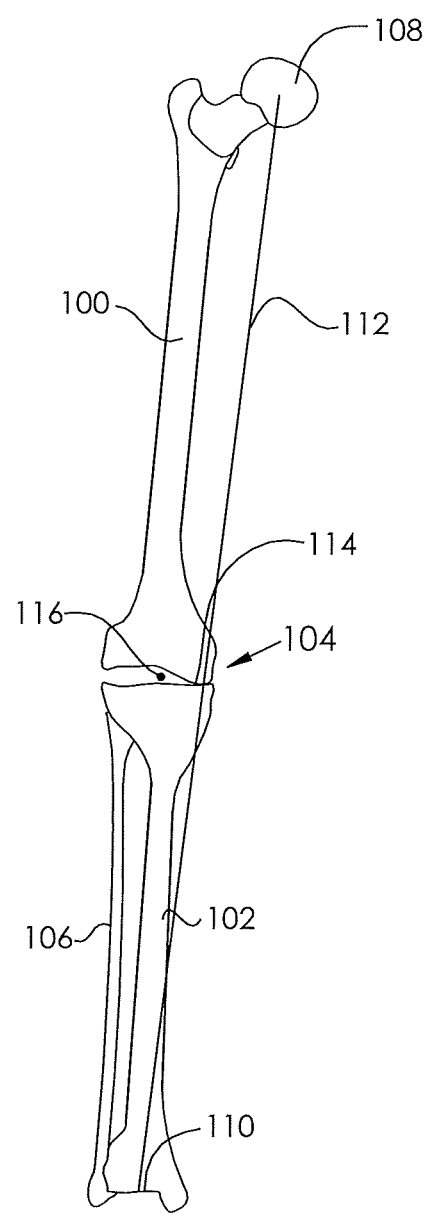
FIG. 1                    FIG. 2

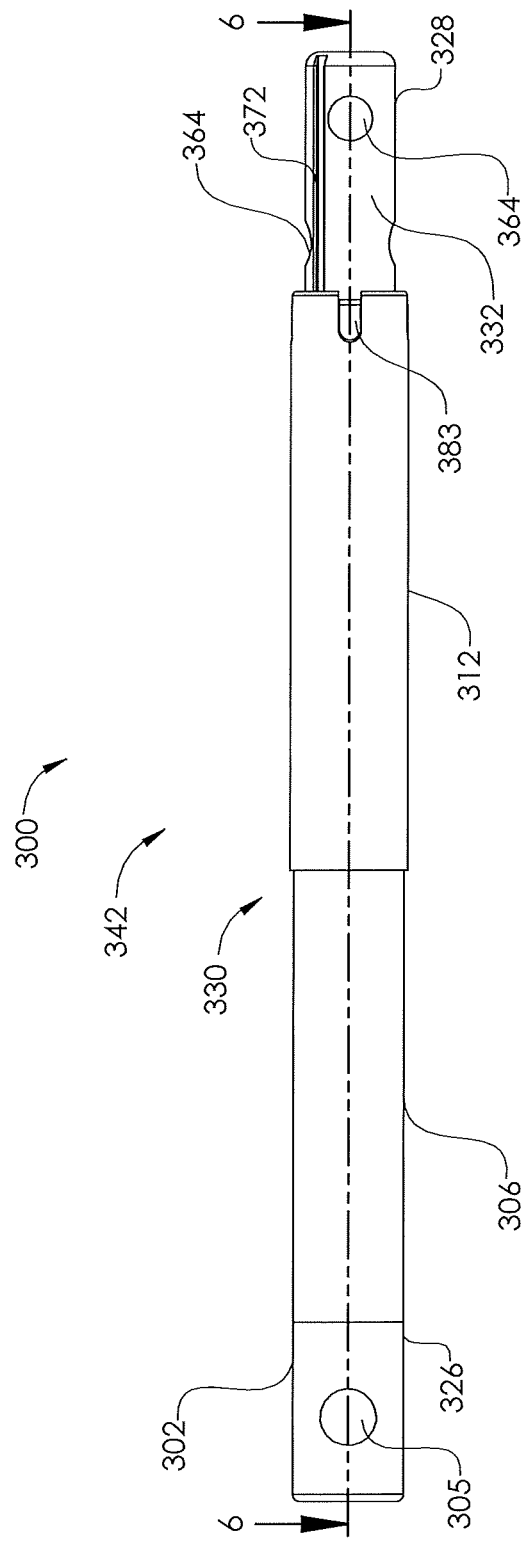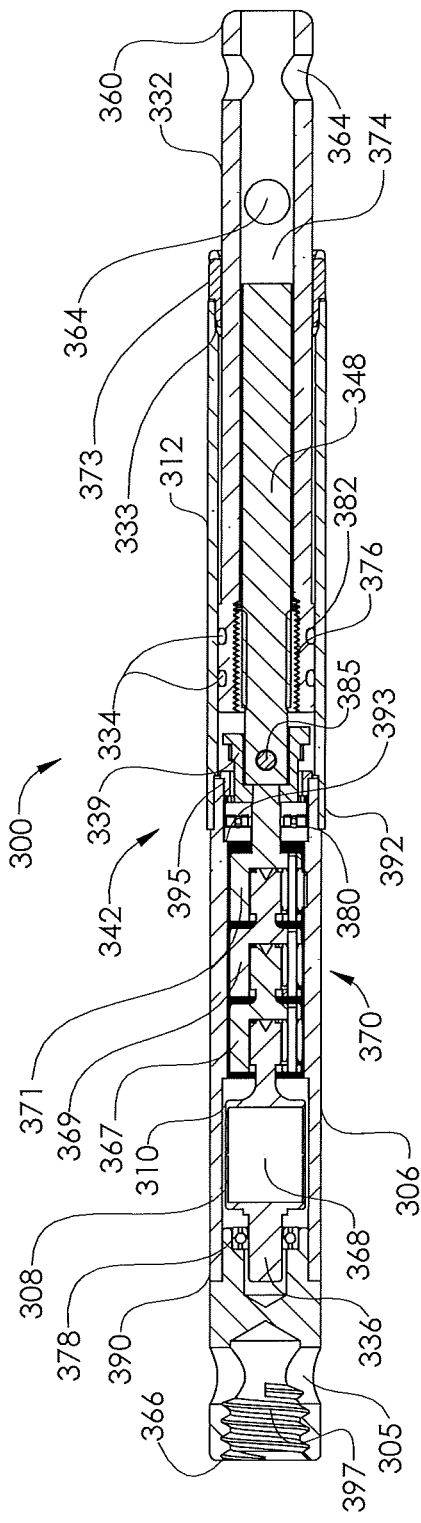

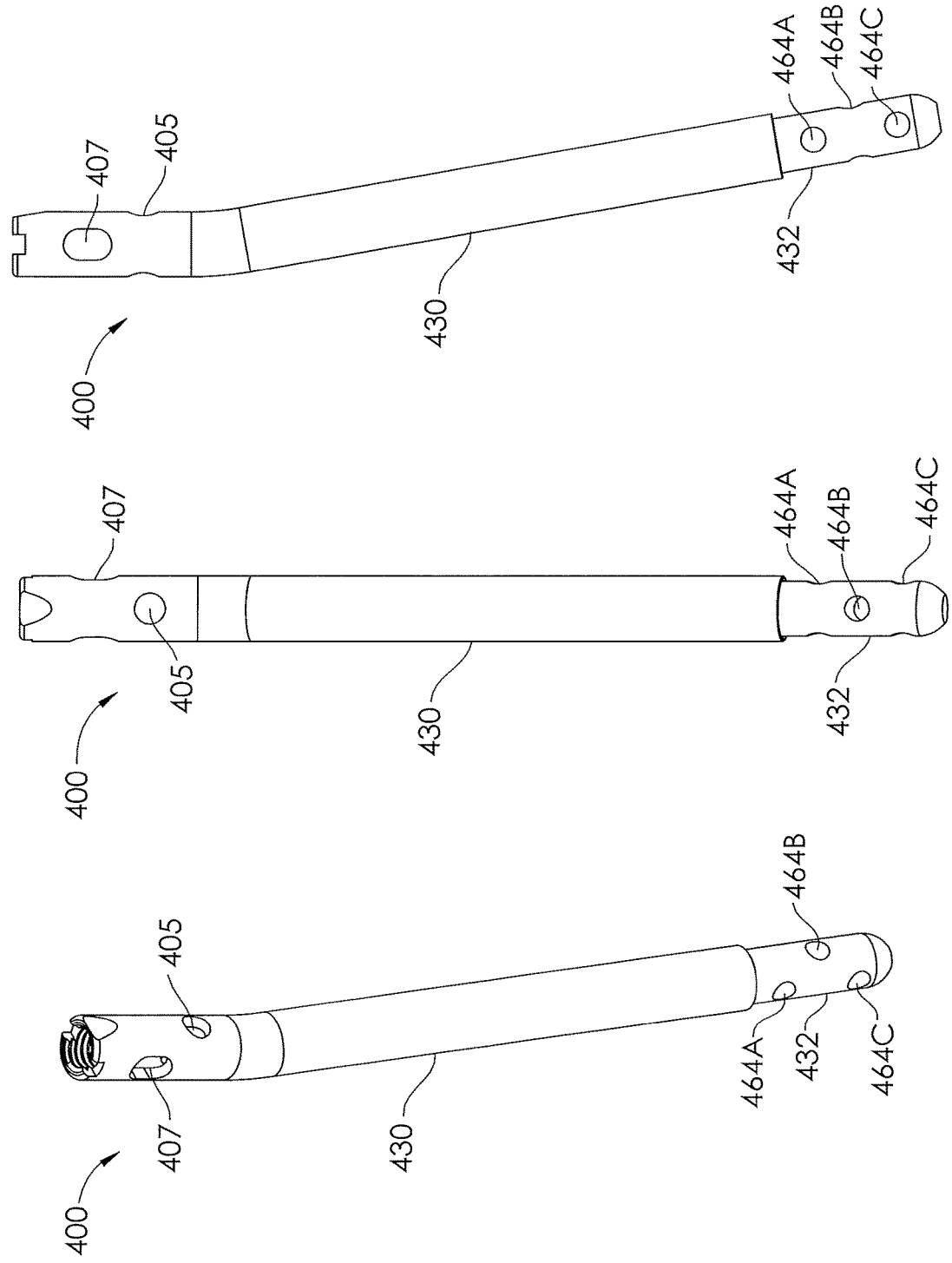

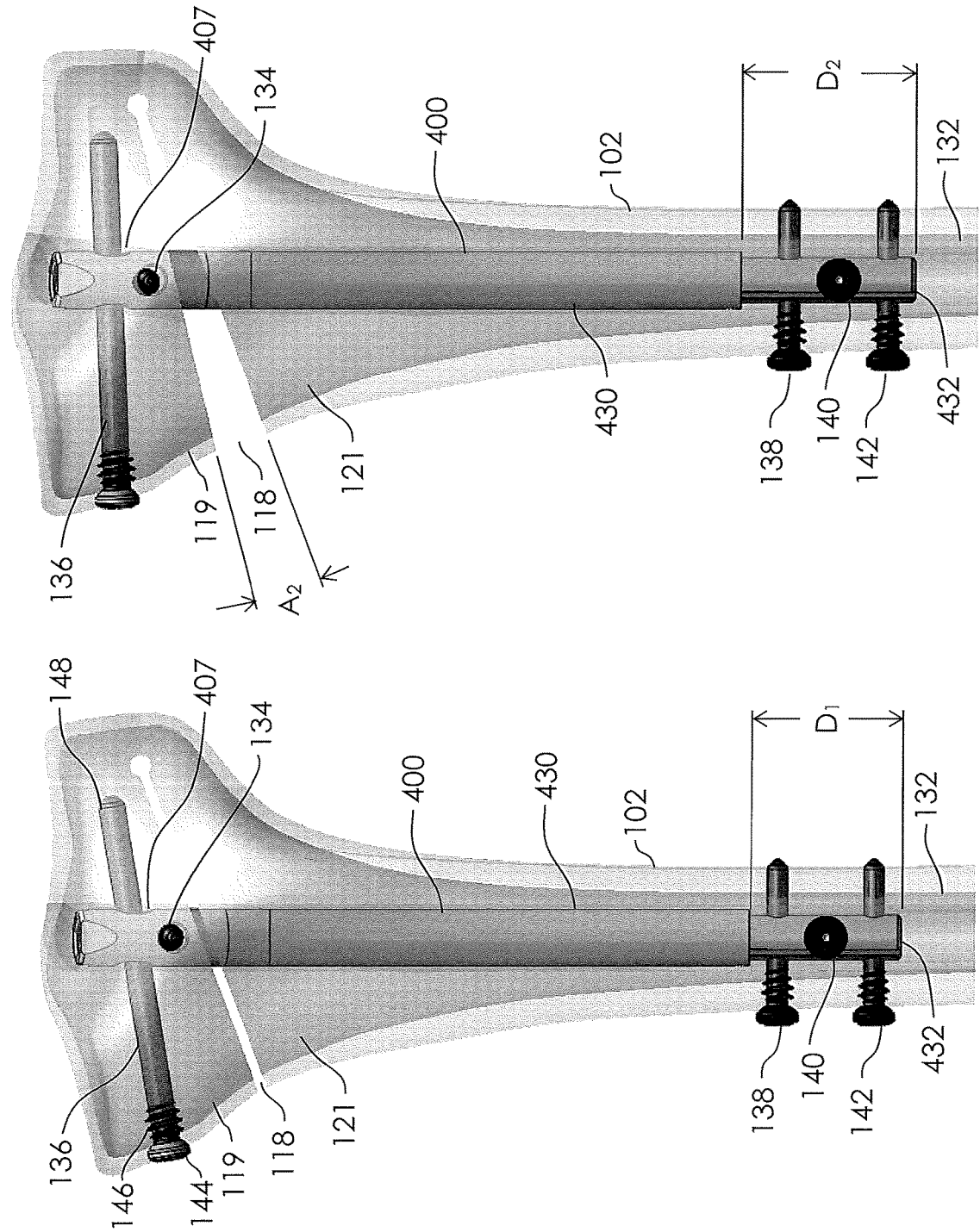

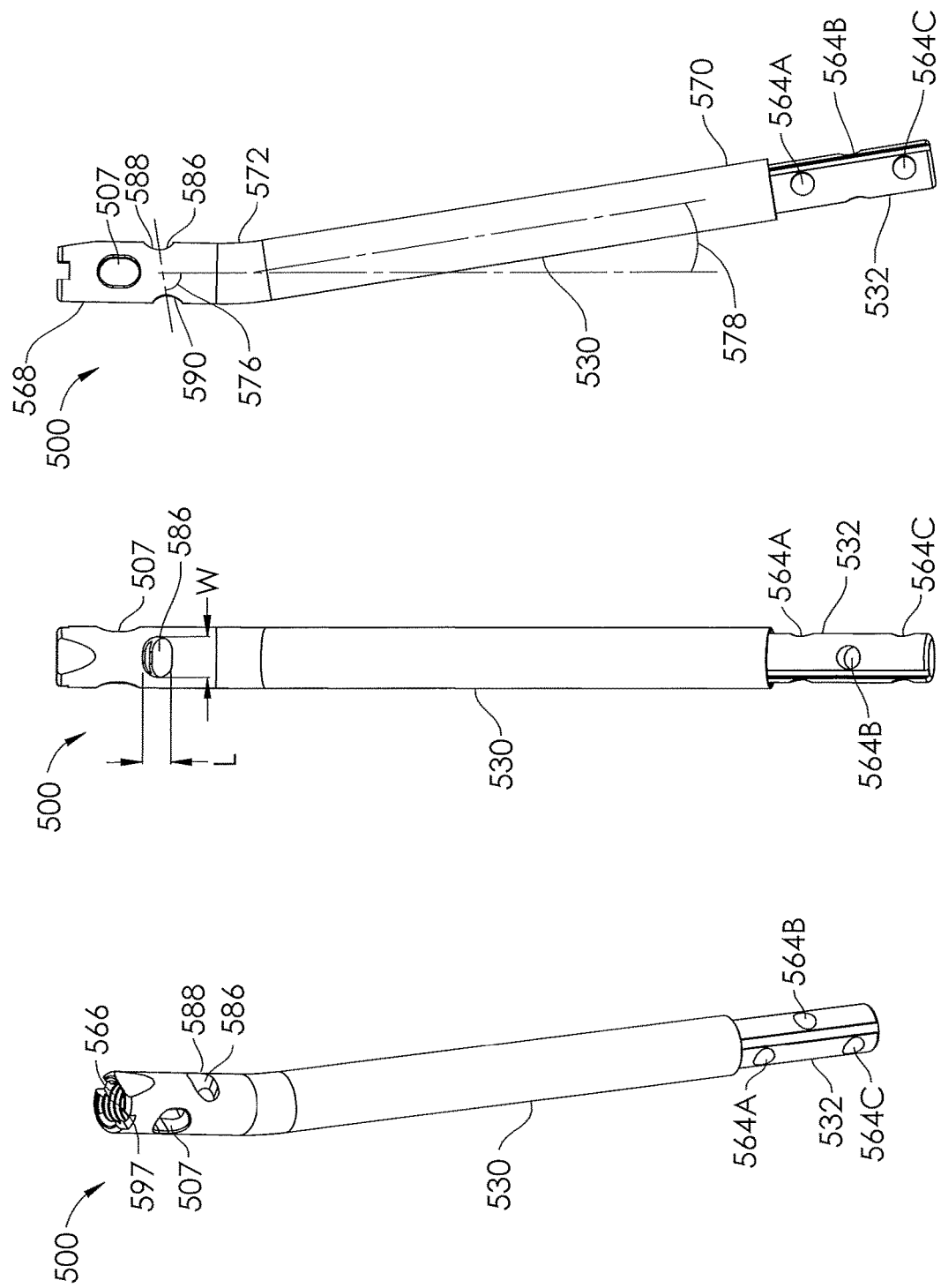

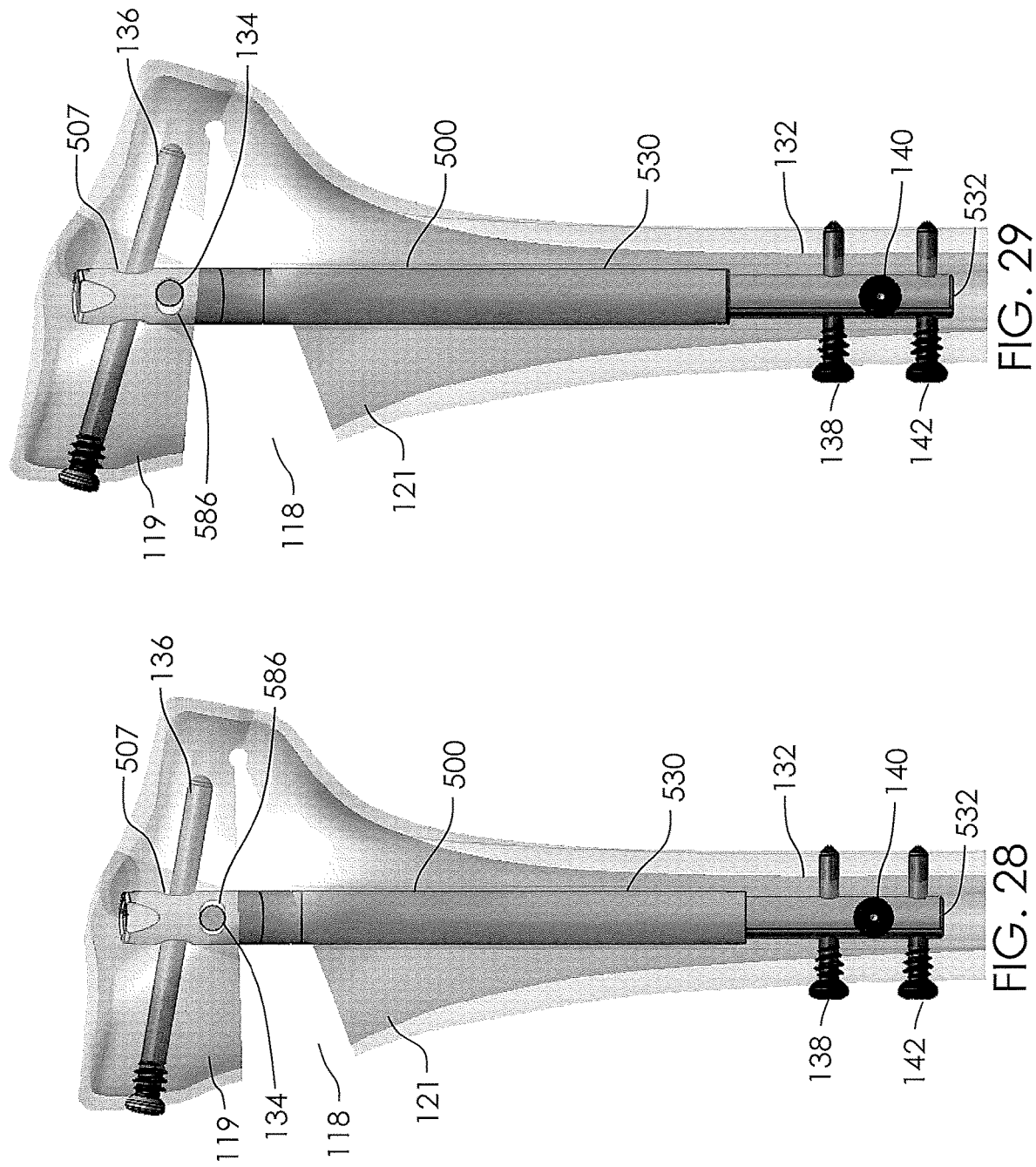

ADJUSTABLE DEVICES FOR TREATING ARTHRITIS OF THE KNEE

CROSS REFERENCES TO RELATED APPLICATIONS

This application is a continuation of U.S. patent application Ser. No. 16/812,114, filed on Mar. 6, 2020, which is a continuation of U.S. patent application Ser. No. 15/953,453 (now U.S. Pat. No. 10,617,453), filed on Apr. 15, 2018, which is a continuation of International Application PCT/US2016/057371, filed on Oct. 17, 2016, which claims priority to U.S. Provisional Patent Application No. 62/242,931, filed on Oct. 16, 2015, the entire disclosures of which are incorporated herein by reference.
Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating knee osteoarthritis.

DESCRIPTION OF THE RELATED ART

Knee osteoarthritis is a degenerative disease of the knee joint that affects a large number of patients, particularly over the age of 40. The prevalence of this disease has increased significantly over the last several decades, attributed partially, but not completely, to the rising age of the population as well as the increase in obesity. The increase may also be due to the increase in highly active people within the population. Knee osteoarthritis is caused mainly by long term stresses on the joint that degrade the cartilage covering the articulating surfaces of the bones in the joint, including both the femur and tibia. Oftentimes, the problem becomes worse after a trauma event, but can also be a hereditary process. Symptoms may include pain, stiffness, reduced range of motion, swelling, deformity, and muscle weakness, among others. Osteoarthritis may implicate one or more of the three compartments of the knee: the medial compartment of the tibiofemoral joint, the lateral compartment of the tibiofemoral joint, and/or the patellofemoral joint. In severe cases, partial or total replacement of the knee may be performed to replace diseased portions with new weight bearing surfaces, typically made from implant grade plastics or metals. These operations can involve significant post-operative pain and generally require substantial physical therapy. The recovery period may last weeks or months. Several potential complications of this surgery exist, including deep venous thrombosis, loss of motion, infection, and bone fracture. After recovery, surgical patients who have received partial or total knee replacement must significantly reduce their activity, removing high energy and impact activities, including running and many other sports, completely from their lifestyle.

BRIEF DESCRIPTION OF THE DRAWINGS

FIG. 1 illustrates a desirable alignment of a knee joint.
FIG. 2 illustrates a misaligned knee joint.
FIG. 5 illustrates a non-invasively adjustable wedge osteotomy device.
FIG. 6 illustrates a cross-sectional view of the non-invasively adjustable wedge osteotomy device of FIG. 5 taken along line 6-6.
FIGS. 10-12 illustrate various views of another embodiment of a non-invasively adjustable wedge osteotomy device.
FIG. 18 illustrates a non-invasively adjustable wedge osteotomy device within a tibia in a substantially non-adjusted state.
FIG. 19 illustrates a non-invasively adjustable wedge osteotomy device within a tibia in a first adjusted state.
FIGS. 23-25 illustrate various views of another embodiment of a non-invasively adjustable wedge osteotomy device.
FIGS. 27-29 illustrate the non-invasively adjustable wedge osteotomy device of FIG. 23 within a tibia in various states of adjustment.

SUMMARY OF THE INVENTION

Figure 4:
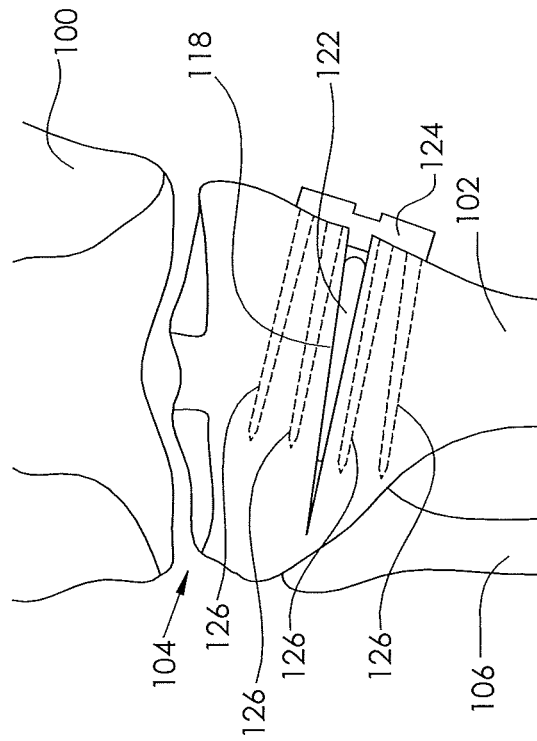
FIG. 4 illustrates an open wedge technique with bone graft inserted and a plate attached.

In a first embodiment, the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole and a second anchor hole, the first anchor hole configured to pass a first anchor for coupling the adjustable implant to a first portion of bone and the second anchor hole configured for to pass a second anchor for coupling the adjustable implant to the first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; and wherein the first anchor hole is configured to allow the first anchor to pivot in at least a first angular direction and the second anchor hole is configured to allow the second anchor to translate in at least a first translation direction.

In a second embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; and a driving element configured to be remotely operable to telescopically displace the inner shaft in relation to the outer housing; wherein the first anchor comprises a first end portion configured to slide within the slot and into cortical bone at a first side of the first portion of bone, a second end portion configured to slide within the slot and into cortical bone at a second side of the first portion of bone, and an intervening portion configured to reside within the first anchor hole.

In a third embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone, wherein the first anchor hole is configured to allow the first anchor to pivot in at least a first angular direction, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; and wherein the at least one of the outer housing and inner shaft additionally includes two engagement portions configured to rotatably engage a curved anchor.

In a fourth embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone wherein the first anchor hole is configured to allow the first anchor to pivot in at least a first angular direction, the inner shaft configured to couple to a second portion of bone that is separated or separable from the first portion of bone; and a driving element configured to rotate a screw threadingly coupled to a nut, the nut comprising an extreme portion configured to contact a location on the first anchor when the first anchor is within the first anchor hole, such that remote actuation of the drive element causes the screw to rotate and to longitudinally displace the nut, thus causing the first anchor to pivot in the first rotational direction.

In a fifth embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one end of the non-invasively adjustable implant associated with a first anchor hole, the first anchor hole configured to pass a first anchor for coupling the adjustable implant to a first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; wherein the at least one end of the non-invasively adjustable implant is rotatably coupled to at least one of the outer housing or the inner shaft.

DETAILED DESCRIPTION

In view of the ramifications of partial and/or total knee replacement surgery, it may be advantageous to intervene early in the progression of a patient's arthritis. In such cases, knee replacement surgery may be delayed or even precluded. Osteotomy surgeries may be performed on the femur or tibia to change the angle between the femur and tibia thereby adjusting the stresses on the different portions of the knee joint. In closed wedge or closing wedge osteotomy, an angled wedge of bone may be removed and the remaining surfaces fused together to create a new, improved bone angle. In open wedge osteotomy, a cut may be made in the bone and the edges of the cut opened to create a new angle. Bone graft material may advantageously be used to fill in the new opened wedge-shaped space, and a plate may be attached to the bone with bone screws to provide additional structural support. However, obtaining a desired or correct angle during either a closed wedge or open wedge osteotomy, as described above, is almost always suboptimal. Furthermore, even if the resulting angle is approximately to that desired, there may be a subsequent loss of correction angle. Other potential complications that may be experienced when using these techniques include nonunion and material failure.

FIG. 1 illustrates a correct/healthy alignment of a femur 100, tibia 102, and knee joint 104. In such correct alignments, a hip joint (at a femur head 108), knee joint 104, and ankle joint (at the midline of distal tibia 110) are generally disposed along a single line 112, known as the mechanical axis. A fibula 106 is shown alongside the tibia 102. By contrast to the knee joint 104 of FIG. 1, the knee joint 104 of FIG. 2 is shown in an arthritic state, in which the knee's medial compartment 114 (medial meaning situated in or disposed toward the middle or center) has been compromised, causing the line 112 to pass medially off the center of the knee joint 104.

Figure 3:
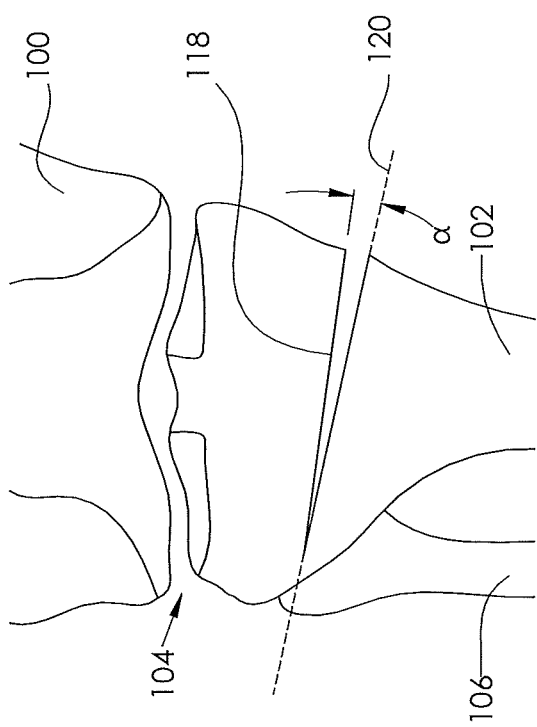
FIG. 3 illustrates an open wedge technique in a tibia.

FIG. 3 illustrates an open wedge osteotomy 118 formed by making a cut along a cut line 120, and opening a wedge angle α. FIG. 4 illustrates the final setting of this open wedge by the placement of bone graft material 122 within the open wedge osteotomy 118, and then placement of a plate 124, which is then secured to the tibia 102 with tibial screws 126. The increase in the wedge angle α can also be described as moving away from varus and/or moving towards valgus.

Figure 7:
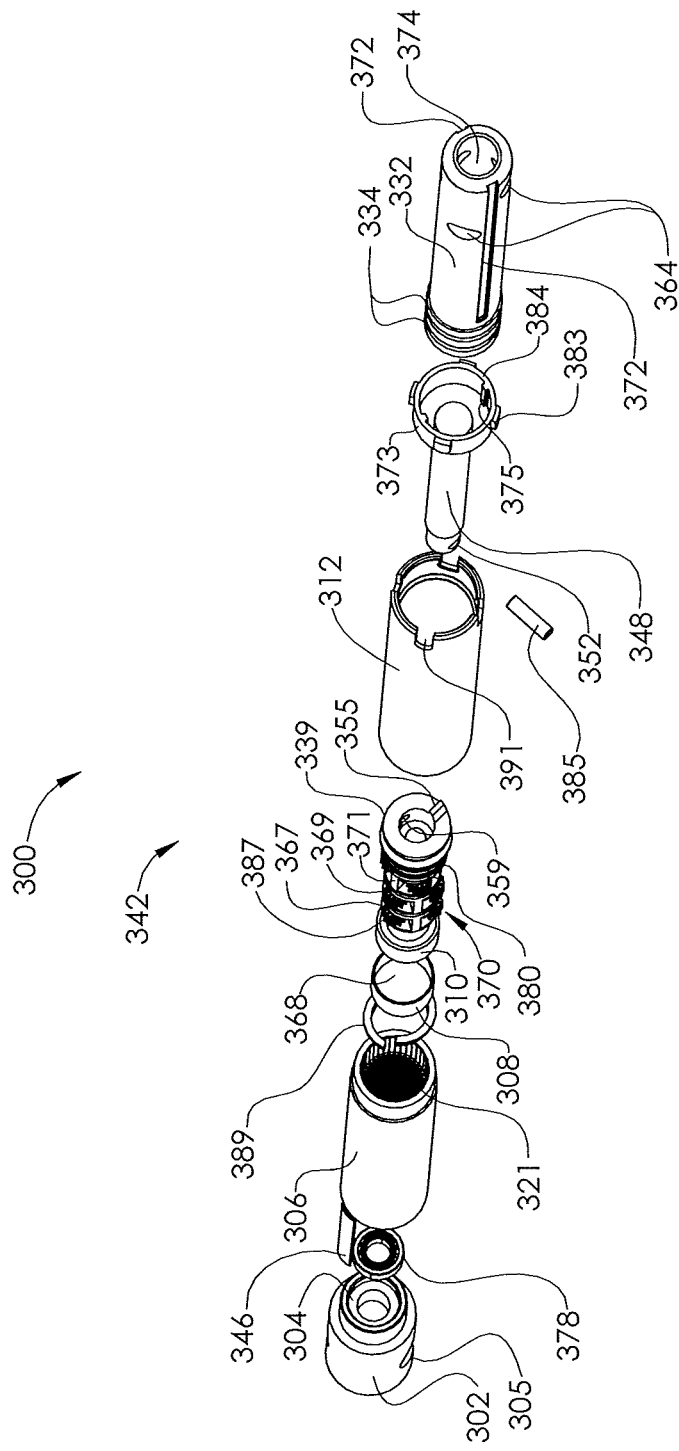
FIG. 7 illustrates an exploded view of the non-invasively adjustable wedge osteotomy device of FIG. 5.

FIGS. 5-7 illustrate a non-invasively adjustable wedge osteotomy device 300 comprising a magnetically adjustable actuator 342, and having a first end 326 and a second end 328. An inner shaft 332 having a cavity 374 is telescopically coupled to or within an outer housing 330 that comprises a distraction housing 312 and a gear housing 306. At least one proximal transverse hole 305 passes through an end cap 302 located at the first end 326 of the magnetically adjustable actuator 342. The at least one proximal transverse hole 305 allows passage of a bone screw, or other fixation device, therethrough to fix the adjustable wedge osteotomy device 300 to the bone in which it is implanted, e.g., the tibia 102. The end cap 302 may be sealably secured to the gear housing 306 by a circumferential weld joint 390. In some embodiments, the end cap 302 may be secured to the gear housing 306 by any appropriate method of fixation, such as friction, glues, epoxies, or any type of welding. In yet other embodiments, the end cap 302 and the gear housing 306 may be formed monolithically, or in one piece. A second weld joint 392 sealably secures the distraction housing 312 to the gear housing 306. In some embodiments, the distraction housing 312 may be secured to the gear housing 306 by any appropriate method of fixation, such as friction, glues, epoxies, or any type of welding. In yet other embodiments, the distraction housing 312 and the gear housing 306 may be formed monolithically, or in one piece. One or more distal transverse holes 364 pass through the inner shaft 332. The one or more distal transverse holes 364 allows passage of a bone screw, or other fixation device, therethrough to fix the adjustable wedge osteotomy device 300 to the bone in which it is implanted, e.g., the tibia 102. For example, the one or more distal transverse holes 364 and the at least one proximal transverse hole 305 allow passage of at least one locking screw. Some embodiments use only one distal transverse hole 364 and one proximal transverse hole 305 in order to better allow rotational play between the magnetically adjustable actuator 342 and the locking screws as the magnetically adjustable actuator 342 is adjusted.

In some embodiments, one or more longitudinal grooves 372 in the outer surface of the inner shaft 332 engage with protrusions 375 of an anti-rotation ring 373 (Shown in FIG. 7) to advantageously minimize or inhibit rotational movement between the inner shaft 332 and the distraction housing 312. The anti-rotation ring also engages undercuts 333 within end of the distraction housing 312 at a flat edge 384 of the anti-rotation ring 373. One or more guide fins 383 in the anti-rotation ring 373 can keep the anti-rotation ring 373 rotationally static within cuts 391 in the distraction housing 312.

The contents of the magnetically adjustable actuator 342 may advantageously be protected from bodily fluids. In some embodiments, the contents of the magnetically adjustable actuator 342 are sealed off from the body by one or more o-rings 334 that may reside between the inner shaft 332 and the distraction housing 312. For example, one or more circumferential grooves 382 in the outer surface of the inner shaft 332, for dynamically sealing along the inner surface of the distraction housing 312. The inner shaft 332 may be extended/retracted axially with respect to the outer housing 330, for example, by a lead screw 348 turned by a cylindrical radially poled magnet 368. The cylindrical radially poled magnet 368 is bonded within a first portion of a magnet housing 308 and a second portion of a magnet housing 310 and is rotatably held on one end by pin 336 and a radial bearing 378, which directly engages the counterbore 304 (shown in FIG. 7) of the end cap 302. The second magnet housing 310 is connected to or coupled to a first stage 367 of a planetary gear system 370.

In some embodiments, the planetary gear system 370 may have one stage, two stages, three stages, four stages or even five stages. In other embodiments, more than five stages may be included, if required. The embodiment of the planetary gear system 370 shown in FIG. 6 has three stages. Regardless of how many stages are included in the device, they may work generally according to the description provided below. The planet gears 387 of the three planetary gear system 370 turn within inner teeth 321 within the gear housing 306 (shown in FIG. 7). The first stage 367 outputs to a second stage 369, and the second stage 369 outputs to a third stage 371. The last or third stage 371 is coupled to the lead screw 348. In some embodiments, the last or third stage 371 is coupled to the lead screw 348 by a coupling that allows some degree of axial play between the third stage 371 and the lead screw 348, such as, for example, by a locking pin 385 that passes through holes 352 in both the output of the third stage 371 and in the lead screw 348. Alternatively, the third stage 371 may output directly to the lead screw 348. The lead screw 348 threadingly engages with a nut 376 that is bonded within the cavity 374 of the inner shaft 332. Each stage of the planetary gear system 370 incorporates a gear ratio. In some embodiments, the gear ratio may be 2:1, 3:1, 4:1, 5:1, or 6:1. In other embodiments, the gear ratio may be even higher than 6:1, if necessary. The overall gear ratio produced by the planetary gear system is equal to each side of the gear ratio raised to the number of stages. For example, a three (3)-stage system having a gear ratio of 4:1, such as that shown in FIG. 6, has a final ratio of 4*4*4:1*1*1, or 64:1. A 64:1 gear ratio means that 64 turns of the cylindrical radially poled magnet 368 cause a single turn of the lead screw 348. In the same way, a two (2)-stage system having a gear ratio of 3:1 has a final ratio of 3*3:1*1, or 9:1. In some embodiments, the planetary gear system 370 includes stages with different gear ratios. For example, a three-stage planetary gear system 370 could include a first stage having a gear ratio of 4:1, a second stage having a gear ratio of 3:1, and a third stage having a ratio of 2:1: that system has a final ratio of 4*3*2:1*1*1, or 24:1. It may be desirable to include structural features in the housing to absorb axial loads on the cylindrical radially-poled magnet and/or the planetary gear system 370.

In some embodiments, one or more thrust bearings may be used to absorb axial loads. For example, thrust bearing 380 may be held loosely in the axial direction between ledges in the gear housing 306. The thrust bearing 380 is held between a ledge 393 in the gear housing 306 and an insert 395 at the end of the gear housing 306. The thrust bearing 380 advantageously protects the cylindrical radially poled magnet 368, the planetary gear system 370, the magnet housings 308 and 310, and the radial bearing 378 from unacceptably high compressive forces.

In some embodiments, a lead screw coupler 339 may be held to the lead screw 348 by the pin 385 passing through hole 359. The lead screw coupler 339 may include a ledge 355, which is similar to an opposing ledge (not shown) at the base of the lead screw 348. In these embodiments, when the inner shaft 332 is retracted to the minimum length, the ledge at the base of the lead screw 348 abuts the ledge 355 of the lead screw coupler, advantageously preventing the lead screw 348 from being jammed against the nut with too high of a torque.

A maintenance member 346, or magnetic brake, comprising a magnetic material, may be included (e.g., bonded) within the gear housing 306 adjacent to the cylindrical radially poled magnet 368. In such embodiments, the maintenance member 346 can attract a pole of the cylindrical radially poled magnet 368 to minimize unintentional rotation of the cylindrical radially poled magnet 368 (e.g., turning when not being adjusted by the external adjustment device 1180, such as during normal patient movement or activities). The maintenance member 346 may advantageously exert a lesser magnetic force on the cylindrical radially poled magnet 368 than the external adjustment device 1180. As such, the maintenance member holds the cylindrical radially poled magnet 368 substantially rotationally fixed most of the time (e.g., when not being adjusted during distraction/retraction). But, when the external adjustment device 1180 is used, the stronger forces of the external adjustment device 1180 overcome the force generated by the maintenance member 346 and turn the cylindrical radially poled magnet 368. In some embodiments, the maintenance member 346 is '400 series' stainless steel. In other embodiments, the maintenance member 346 can be any other appropriate magnetically permeable material.

The non-invasively adjustable wedge osteotomy device 300 has the capability to increase or decrease its length by extending the inner shaft 332 out from the distraction housing 312 and retracting the inner shaft 332 into the distraction housing 312, respectively. The non-invasively adjustable wedge osteotomy device 300 has a length of travel defined as the difference between its length when fully extended and its length when fully retracted. In some embodiments, the adjustable wedge osteotomy device 300 has a length of travel of less than about 30 mm, less than about 24 mm, less than about 18 mm, less than about 12 mm, and less than about 6 mm. In other embodiments, the non-invasively adjustable wedge osteotomy device 300 has a length of travel greater than 30 mm, or any other length of travel that is clinically meaningful. Interaction between the non-invasively adjustable wedge osteotomy device 300 and the magnetic handpiece 1178 of the external adjustment device 1180 that causes rotation of the cylindrical radially poled magnet 368 causes the inner shaft 332 to retract (depending on the direction of magnet rotation) into the distraction housing 312 thereby producing a compressive force, or causes the inner shaft 332 to extend (depending on the direction of magnet rotation) out from the distraction housing. The force that can be produced by the non-invasively adjustable wedge osteotomy device 300 is determined by a number of factors, including: size of cylindrical radially poled magnet 368, size of the maintenance member 346, magnetic force produced by the external adjustment device 1180 (determined by the size of the magnet(s) of the magnetic handpiece 1178), the distance between the magnetic handpiece 1178 and the cylindrical radially poled magnet 368, the number of gear stages, the gear ratio of each gear stage, internal frictional losses within the non-invasively adjustable wedge osteotomy device 300, etc. In some embodiments, the non-invasively adjustable wedge osteotomy device 300 in a clinical setting (i.e., implanted into an average patient) is capable of generating up to about 300 lbs., up to about 240 lbs., up to about 180 lbs., and up to about 120 lbs., or any other force that is clinically meaningful or necessary. In some embodiments, the magnetic handpiece 1178 of the external adjustment device 1180, placed so that its magnets 1186 are about one-half inch from the cylindrical radially poled magnet 368, can achieve a distraction force of about 240 pounds.

Many components of the non-invasively adjustable wedge osteotomy device may be made from Titanium, Titanium alloys (e.g., Titanium-6Al-4V), Cobalt Chromium, Stainless Steel, or other alloys. The diameter of the non-invasively adjustable wedge osteotomy device 300 is dictated by the size of the medullary canal 130 in the patient's tibia 102. While the medullary canal 130 may be enlarged through reaming or any other appropriate technique, it is generally desirable to select a non-invasively adjustable wedge osteotomy device 300 having a diameter approximately the same as or slightly smaller than the diameter of medullary canal 130. In some embodiments the non-invasively adjustable wedge osteotomy device 300 has a diameter of less than about 16 mm, less than about 14 mm, less than about 12 mm, less than about 10 mm, less than about 8 mm, or less than about 6 mm. In some embodiments, any other diameter that is clinically meaningful to a given patient may be used.

The non-invasively adjustable wedge osteotomy device 300 may be inserted by hand or may be attached to an insertion tool (for example a drill guide). In some embodiments, an interface 366 comprising an internal thread 397 is located in the end cap 302 for reversible engagement with male threads of an insertion tool. Alternatively, such engagement features may be located on the end 360 of the inner shaft 332. In other embodiments, a tether (e.g., a detachable tether) may be attached to either end of the non-invasively adjustable wedge osteotomy device 300, so that it may be easily removed if placed incorrectly.

Figure 8:
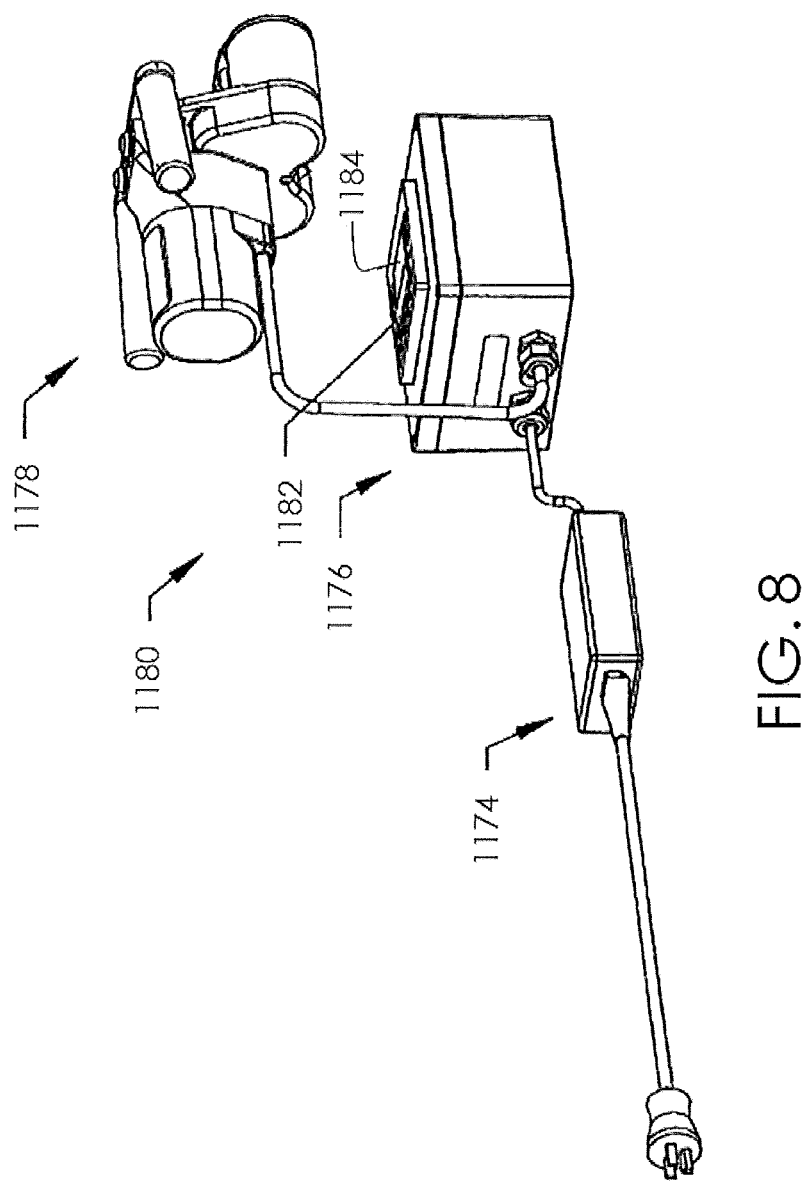
FIG. 8 illustrates an external adjustment device.

FIG. 8 illustrates an embodiment of an external adjustment device 1180 that is used to non-invasively adjust the devices and systems described herein. As shown in FIG. 8, the external adjustment device 1180 may include a magnetic handpiece 1178, a control box 1176, and a power supply 1174. The control box 1176 may include a control panel 1182 having one or more controls (buttons, switches, or tactile feedback mechanisms (i.e., any feedback mechanism that can be sensed using the sense of touch, including, for example, heat, vibration, change in texture, etc.), motion, audio or light sensors) and a display 1184. The display 1184 may be visual, auditory, tactile, the like or some combination of the aforementioned features. The external adjustment device 1180 may contain software that allows input by/from the physician.

Figure 9:
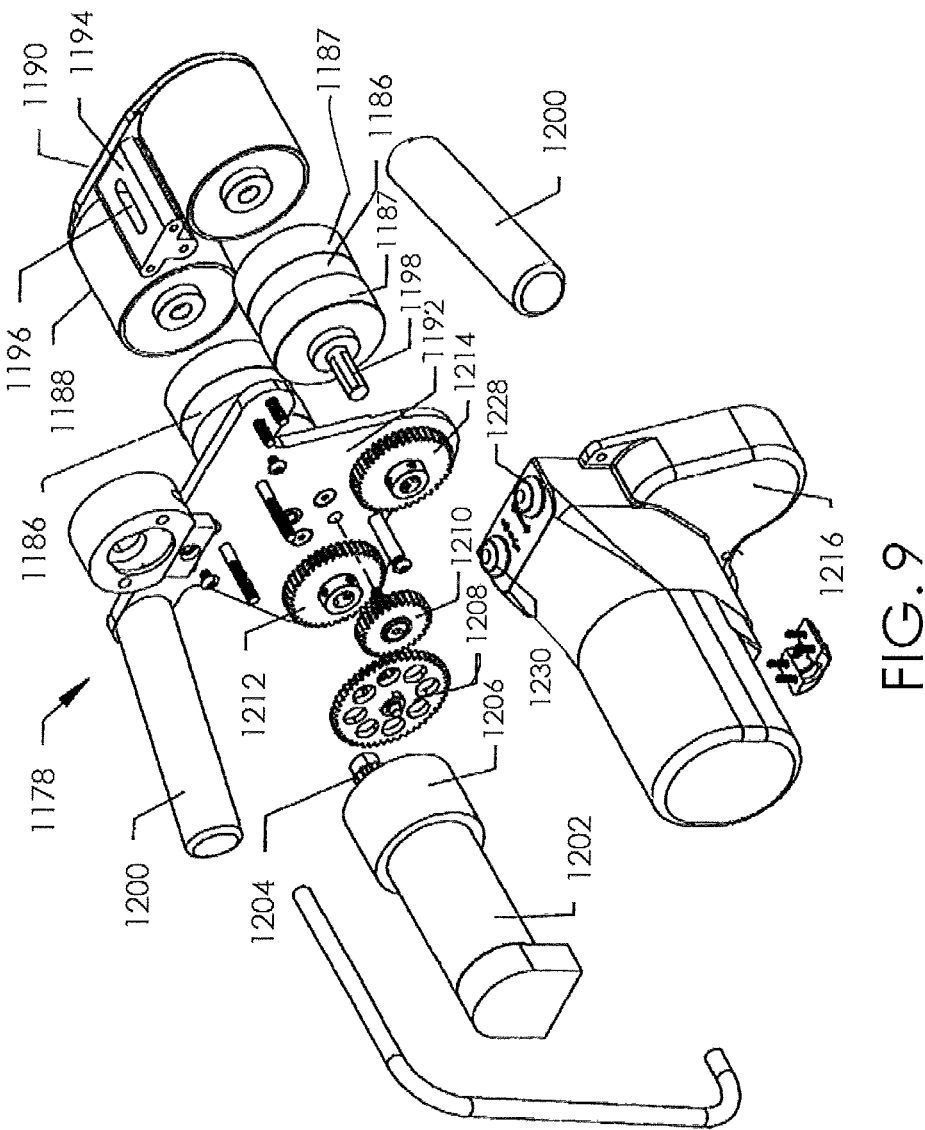
FIG. 9 illustrates an exploded view of the magnetic handpiece of the external adjustment device of FIG. 8.

FIG. 9 shows a detail of an embodiment of the magnetic handpiece 1178 of the external adjustment device 1180. The magnetic handpiece 1178 may include a plurality of magnets 1186, including 6 magnets, 5 magnets, 4 magnets, 3 magnets, or 2 magnets. In some embodiments, the magnetic handpiece 1178 may have only a single magnet. The magnets 1186 may have any of a number of shapes, including, for example, ovoid, cylindrical, etc. FIG. 9 illustrates a magnetic handpiece 1178 that includes two (2) cylindrical magnets 1186. The magnets 1186 can be rare earth magnets (such as Neodymium-Iron-Boron), and can in some embodiments be radially poled. In some embodiments, the magnets 1186 have 2 poles, 4 poles, or 6 poles. In other embodiments, the magnets 1186 have more than 6 poles. The magnets 1186 may be bonded or otherwise secured within magnetic cups 1187. The magnetic cups 1187 each includes a shaft 1198 that is attached to a first magnet gear 1212 and a second magnet gear 1214. The orientation of the poles of each the two magnets 1186 may be generally fixed with respect to each other. For example, the poles may be rotationally locked to one another using a gearing system, which may include a center gear 1210 that meshes with both first magnet gear 1212 and second magnet gear 1214. In some embodiments, the north pole of one of the magnets 1186 turns synchronously with the south pole of the other magnet 1186, at matching clock positions throughout a complete rotation. That configuration provides an improved torque delivery, for example, to radially poled cylindrical magnet 368. Examples of various external adjustment devices that may be used to adjust the various non-invasively adjustable wedge osteotomy devices disclosed herein are described in U.S. Pat. No. 8,382,756, and U.S. patent application Ser. No. 13/172,598, the entirety of which is incorporated by reference herein.

The components of the magnetic handpiece 1178 may be held together between a magnet plate 1190 and a front plate 1192. Components of the magnetic handpiece 1178 may be protected by a cover 1216. The magnets 1186 rotate within a static magnet cover 1188, so that the magnetic handpiece 1178 may be rested directly on the patient without imparting any motion to the external surfaces of the patient (e.g., rubbing against or pulling at the skin of the patient). Prior to use, such as activating a noninvasively adjustable medical device, an operator places the magnetic handpiece 1178 on the patient near the implantation location of the radially poled cylindrical magnet 368. In some embodiments, a magnet standoff 1194 that is interposed between the two magnets 1186 contains a viewing window 1196, to aid in placement of the magnetic handpiece 1178 on the patient. For instance, a mark made on the patient's skin at the appropriate location may be seen through the viewing window 1196 and used to align the magnetic handpiece 1178. To perform a distraction, an operator may hold the magnetic handpiece 1178 by its handles 1200 and depress a distract switch 1228, thereby causing motor 1202 to drive in a first rotational direction. The motor 1202 may have a gear box 1206 which causes the rotational speed of an output gear 1204 to be different from the rotational speed of the motor 1202 (for example, a slower speed or a faster speed). In some embodiments, the gear box 1206 causes the rotational speed of an output gear 1204 to be the same as the rotational speed of the motor. The output gear 1204 then turns a reduction gear 1208 which meshes with center gear 1210, causing it to turn at a different rotational speed than the reduction gear 1208. The center gear 1210 meshes with both the first magnet gear 1212 and the second magnet gear 1214 turning them at the same rate. Depending on the portion of the body where the magnets 1186 of the magnetic handpiece 1178 are located, it may be desirable that the rotation rate of the magnets 1186 be controlled to minimize the induced current density imparted by magnets 1186 and radially poled cylindrical magnet 368 through the tissues and fluids of the body. For example, a magnet rotational speed of 60 revolutions per minute ("RPM") or less is contemplated, although other speeds may be used, such as 35 RPM, or less. At any time, the distraction may be lessened by depressing the retract switch 1230, which can be desirable if the patient feels significant pain, or numbness in the area in which the noninvasively adjustable device has been implanted.

FIGS. 10-12 illustrate a non-invasively adjustable wedge osteotomy device 400 configured for maximizing the amount of potential increase of a wedge angle $\alpha$. As explained with respect to other embodiments (e.g., the non-invasively adjustable wedge osteotomy device 300), an inner shaft 432 is configured to telescopically displace from an outer housing 430, such that the length of the non-invasively adjustable wedge osteotomy device 400 may be increased or decreased. The internal components of the non-invasively adjustable wedge osteotomy device 400 may be configured as is described with respect to other embodiments of the non-invasively adjustable wedge osteotomy device that are disclosed herein. The inner shaft 432 can include one or more transverse holes through which bone anchors or screws can be passed to anchor the device. Such transverse holes may be at any angle with respect to the vertical, and may be at any angle with respect to the horizontal. Desirably, when there is more than one transverse hole, the holes should, ideally, not intersect. In some embodiments, the inner shaft 432 includes three transverse holes 464A, 464B, and 464C for placement of bone screws. In some embodiments, the transverse hole 464B is generally at a 90° angle in relation to each of transverse holes 464A and 464C, which are approximately parallel to each other. Like the inner shaft 432, the outer housing 430 can include one or more transverse holes through which bone anchors or screws can be passed to anchor the device. In some embodiments, the outer housing 430 includes a first transverse hole 405 and a second, slotted transverse hole 407. The first transverse hole 405 may generally be at a 90° angle in relation to the second, slotted transverse hole 407. In some embodiments, the first transverse hole 405 is configured to extend in a generally lateral to medial direction when the non-invasively adjustable wedge osteotomy device 400 is placed within the tibia 102 (lateral meaning situated in or disposed toward the side or sides). In some embodiments, the second, slotted transverse hole 407 is configured to extend in a generally anterior to posterior direction when the non-invasively adjustable wedge osteotomy device 400 is placed within the tibia 102.

Figure 14:
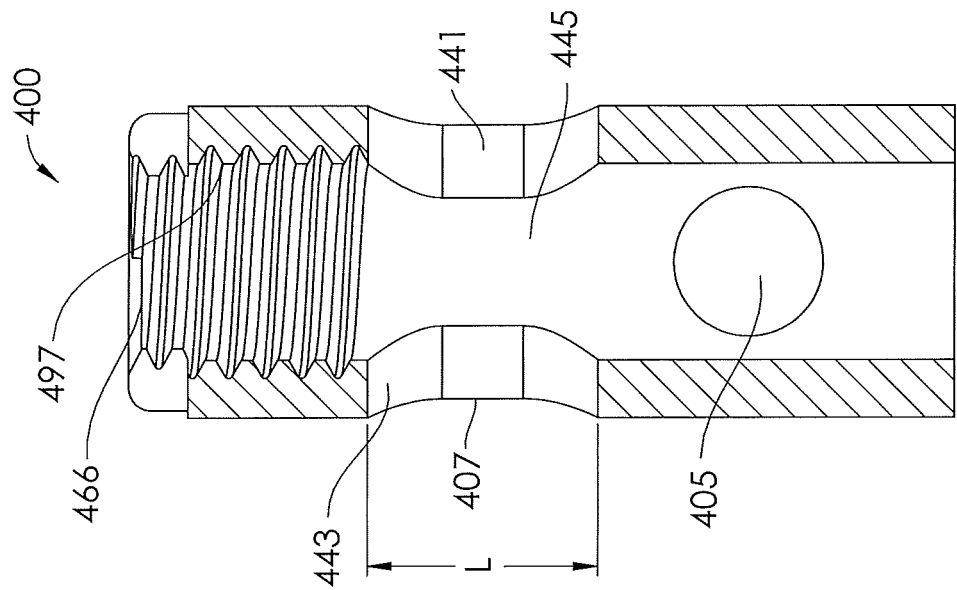
FIG. 14 illustrates a cross-sectional view of the non-invasively adjustable wedge osteotomy device of FIG. 13 taken along line 14-14.
Figure 13:
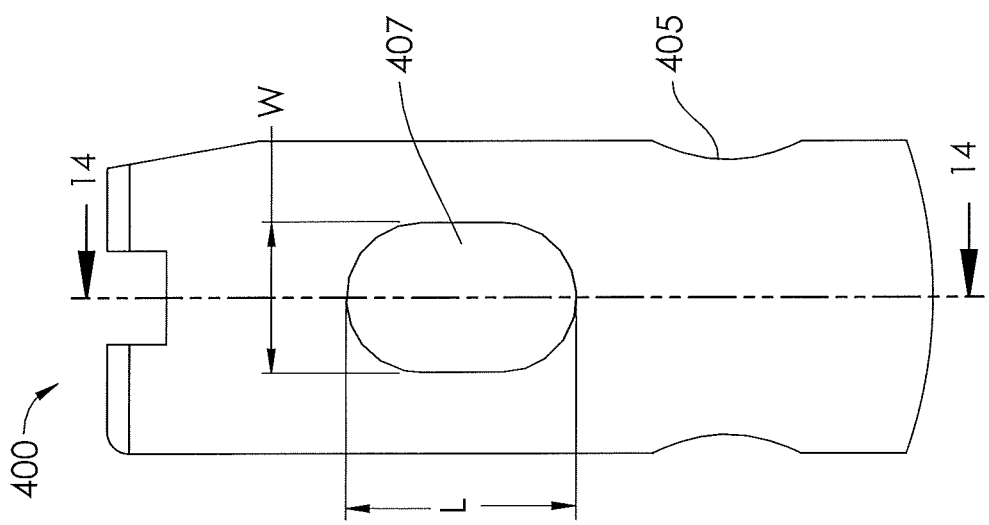
FIG. 13 illustrates an end of the non-invasively adjustable wedge osteotomy device of FIGS. 10-12.

The slotted transverse hole 407 generally extends through two walls 441, 443 of the non-invasively adjustable wedge osteotomy device 400 and through a center cavity 445 (shown in FIGS. 13-14). The slotted transverse hole 407 may have a generally oblong shape, with a length "L" and a width "W". The width W may be configured to be just slightly larger than a bone screw that is used to secure the non-invasively adjustable wedge osteotomy device 400 to a bone, such that the bone screw is able to pass through the slotted transverse hole 407. The length L may be chosen such that the bone screw is able to pivot or angularly displace within the slotted transverse hole 407 up to a desired maximum angulation within a plane (e.g., a plane substantially oriented as the coronal plane). In some embodiments, the ratio of length L to width W (L/W) is always greater than one (1), but is less than about 3, about 2.5, about 2, about 1.5, or about 1.2. By way of example, when the slotted transverse hole 407 is configured to accept a 5 mm bone screw, the width W may be about 5.05 mm-5.25 mm, about 5.1 mm-5.2 mm, or about 5.15 mm, and the length L may be about 6 mm-15 mm, about 7.5 mm-12.5 mm, or about 8 mm-10 mm. FIG. 14 also illustrates an interface 466 having an internal thread 497, which may be used for releasable detachment of an insertion tool.

Figure 51:
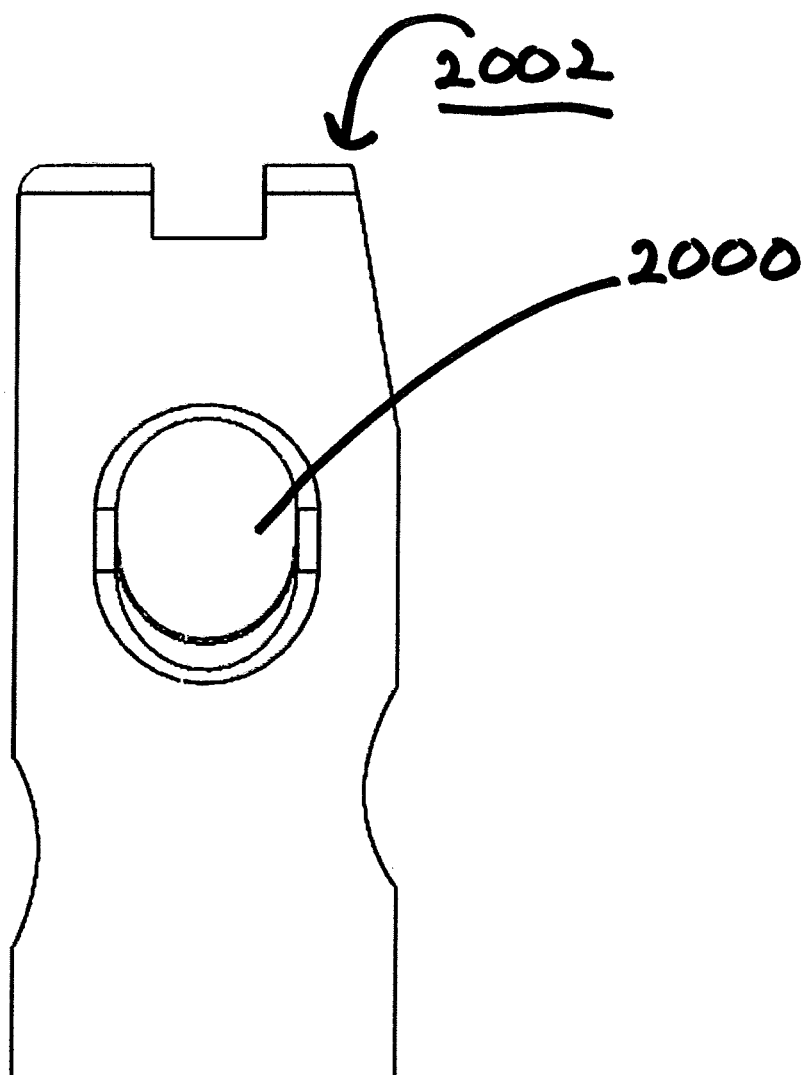
FIG. 51 illustrates a side view of one embodiment of the non-invasively adjustable wedge osteotomy device.
Figure 52:
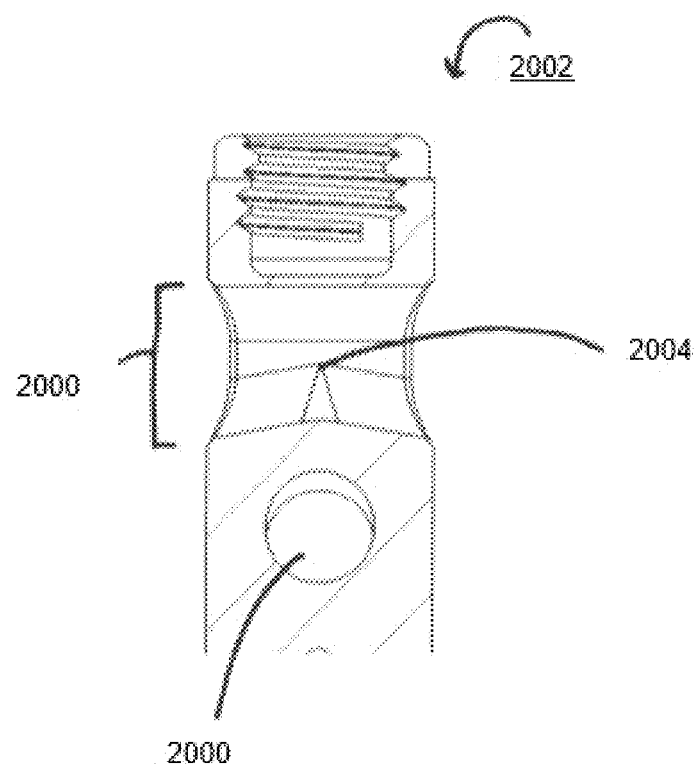
FIG. 52 illustrates a cross sectional view of the non-invasively adjustable wedge osteotomy device of FIG. 51.
Figure 53:
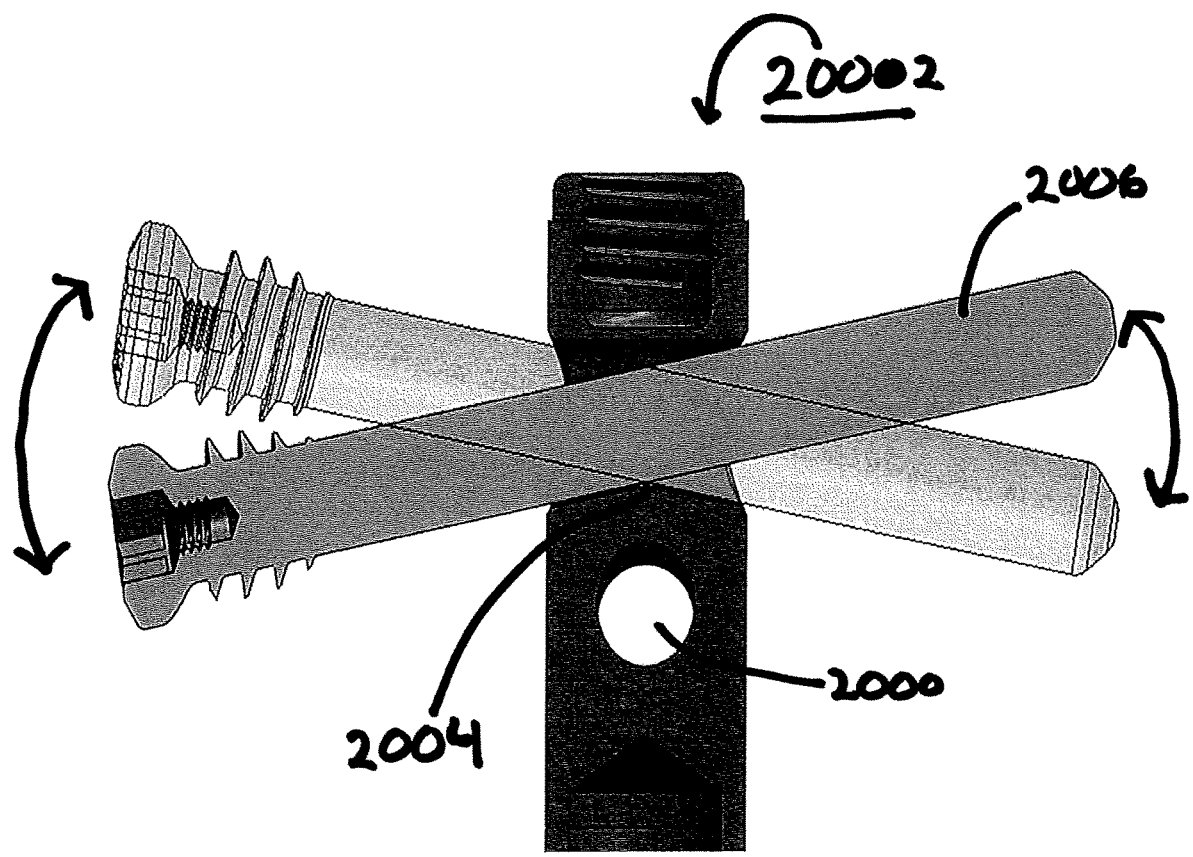
FIG. 53 illustrates yet another view of the non-invasively adjustable wedge osteotomy device of FIGS. 51 and 52.

In another embodiment illustrated by FIGS. 51-53 one or more of the transverse holes 2000 of the non-invasively adjustable wedge osteotomy device 2002 may have a raised portion 2004 substantially centrally located within the transverse holes 2000 upon which a bone anchors or screws 2006 can be passed to anchor the device. In one embodiment, the raised portion 2004 extends generally perpendicular to a longitudinal axis of the transverse holes 2000 such that the lower surface of the transverse hole has a decreasing slope from the raised portion to the exterior in each direction. The raised portion 2002 allows the bone anchors or screws 2006 to pivot providing (as shown by arrows in FIG. 53) greater bone anchor or screw 2006 angulation. The raised portion 2004 may be rounded or it may come to a discrete point within the one or more of the transverse holes 2000. In in embodiment, the bone anchors or screws 2006 may have up to about 40 degrees of movement from a first position to a second position and more specifically may have about 20 degrees of movement from the first position to the second position. The raised portion 2002 may provide an added advantage in that it allows the bone anchor or screw 2006 to achieve its full range of angulation while pivoting about a single point rather than two or more points.

Figures 15, 16:
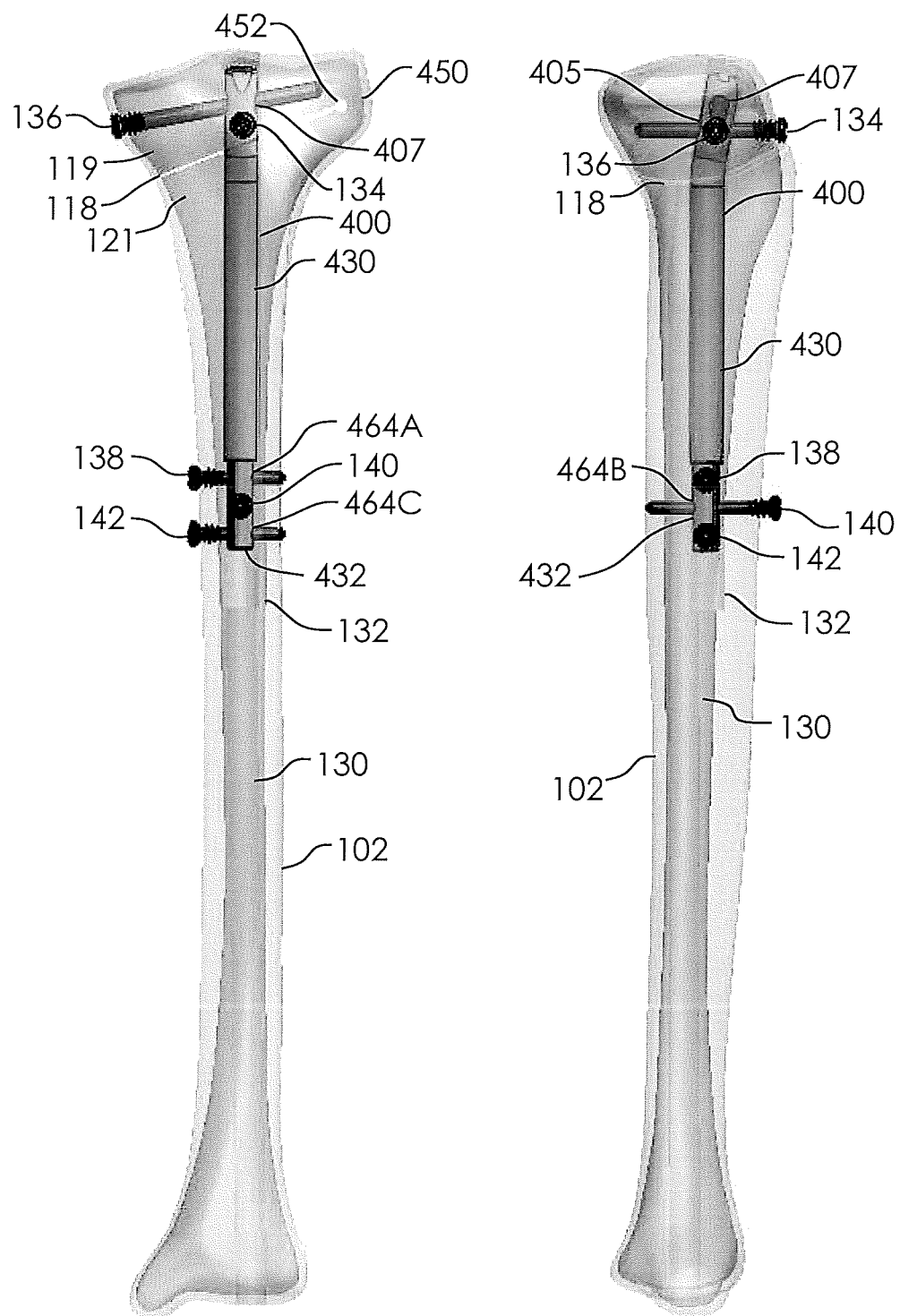
FIG. 15 illustrates a front view of a non-invasively adjustable wedge osteotomy device in place within a tibia.
FIG. 16 illustrates a side view of a non-invasively adjustable wedge osteotomy device in place within a tibia.
Figure 17:
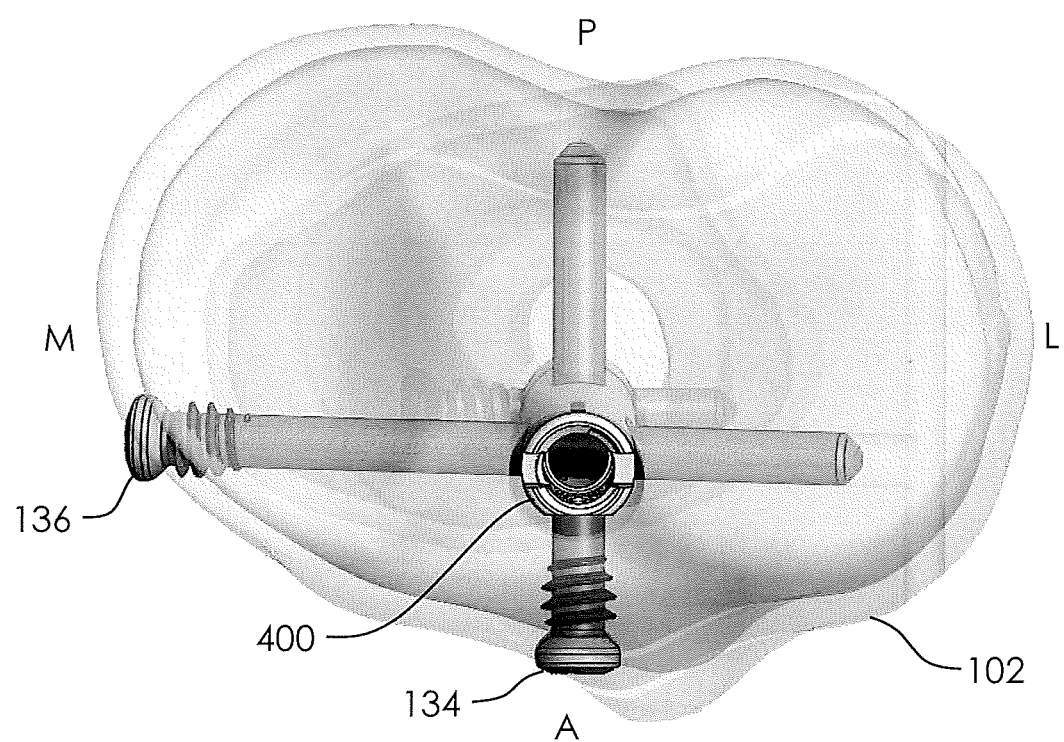
FIG. 17 illustrates a top view of a non-invasively adjustable wedge osteotomy device in place within a tibia.

FIGS. 15-17 show the non-invasively adjustable wedge osteotomy device 400 implanted within a tibia 102 having a medullary canal 130. A hole 132 is drilled along a portion of the length of the medullary canal 130, for example by a series of drills or reamers. An osteotomy 118, which may be either a single cut or a series of cuts (e.g., a wedge), is made in the tibia 102 to separate the tibia 102 into a first portion 119 and a second portion 121. In some cases, a drill hole 452 may be made, and then a blade used to make the cut of the osteotomy 118, up to the point of the drill hole 452. A hinge 450 is thus created at the uncut portion of the tibia 102. Alternatively, the osteotomy 118 may be made entirely through the tibia 102 (such an osteotomy is not shown) and a hinge-like device may be secured to the lateral side of the tibia 102, adjacent the osteotomy. The hinge-like device may comprise or be similar to the Hinge Pediatric Plating System™ sold by Pega Medical of Laval, Quebec, Canada. In this alternative method, the incision and osteotomy could be made from the lateral side instead of the medial side, leaving the medial side without an incision.

Returning to the configurations of FIGS. 15-17, a non-invasively adjustable wedge osteotomy device, such as that shown in FIGS. 10-14, is inserted into the hole 132 and secured to the tibia 102 with bone screws (e.g., two or more bone screws 134, 136, 138, 140, 142). In some embodiments, such as those shown in FIGS. 15-17, the outer housing 430 is secured to the first portion 119 of the tibia 102 with a first bone screw 134 delivered through the first transverse hole 405, and a second bone screw 136 delivered through the slotted transverse hole 407. The inner shaft 432 is secured to the second portion 121 of the tibia 102 with three bone screws 138, 140, 142 delivered through the three transverse holes 464A, 464B, 464C, respectively. As described, the slotted transverse hole 407 may be configured to allow the second bone screw 136 to pivot or rock over an angular range, as will be described further with respect to FIGS. 18-22. As shown in FIGS. 15-17, the first bone screw 134 may be substantially aligned along an Anterior-Posterior axis (i.e., front to back), and the second bone screw 136 may be substantially aligned along the Medial-Lateral axis (i.e., side to side), though in both cases, other degrees of angulation are also contemplated. The non-invasively adjustable wedge osteotomy device 400 is configured to non-invasively distract the first portion 119 of the tibia 102 away from the second portion 121 of the tibia 102, to angularly open the osteotomy 118. With the orientation of the first bone screw 134 and second bone screw 136 shown in FIG. 17, the first bone screw 134 may be free to rotate within the hole 405 (FIG. 16), and the second bone screw 136 may pivot within the slotted transverse hole 407 (FIGS. 15-16).

Figure 20:
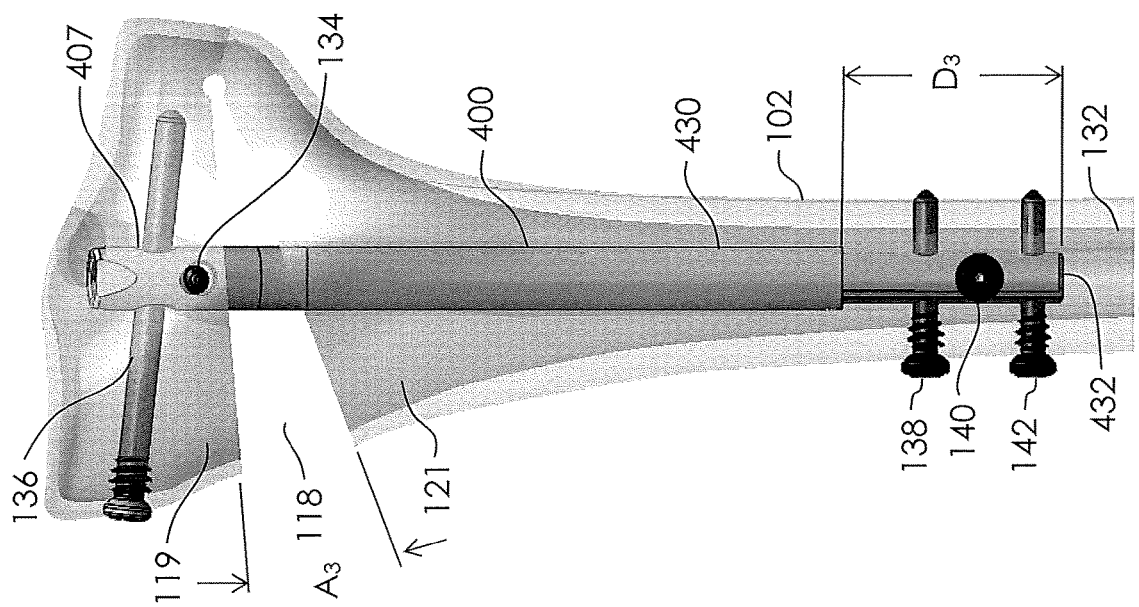
FIG. 20 illustrates a non-invasively adjustable wedge osteotomy device within a tibia in a second adjusted state.
Figure 22:
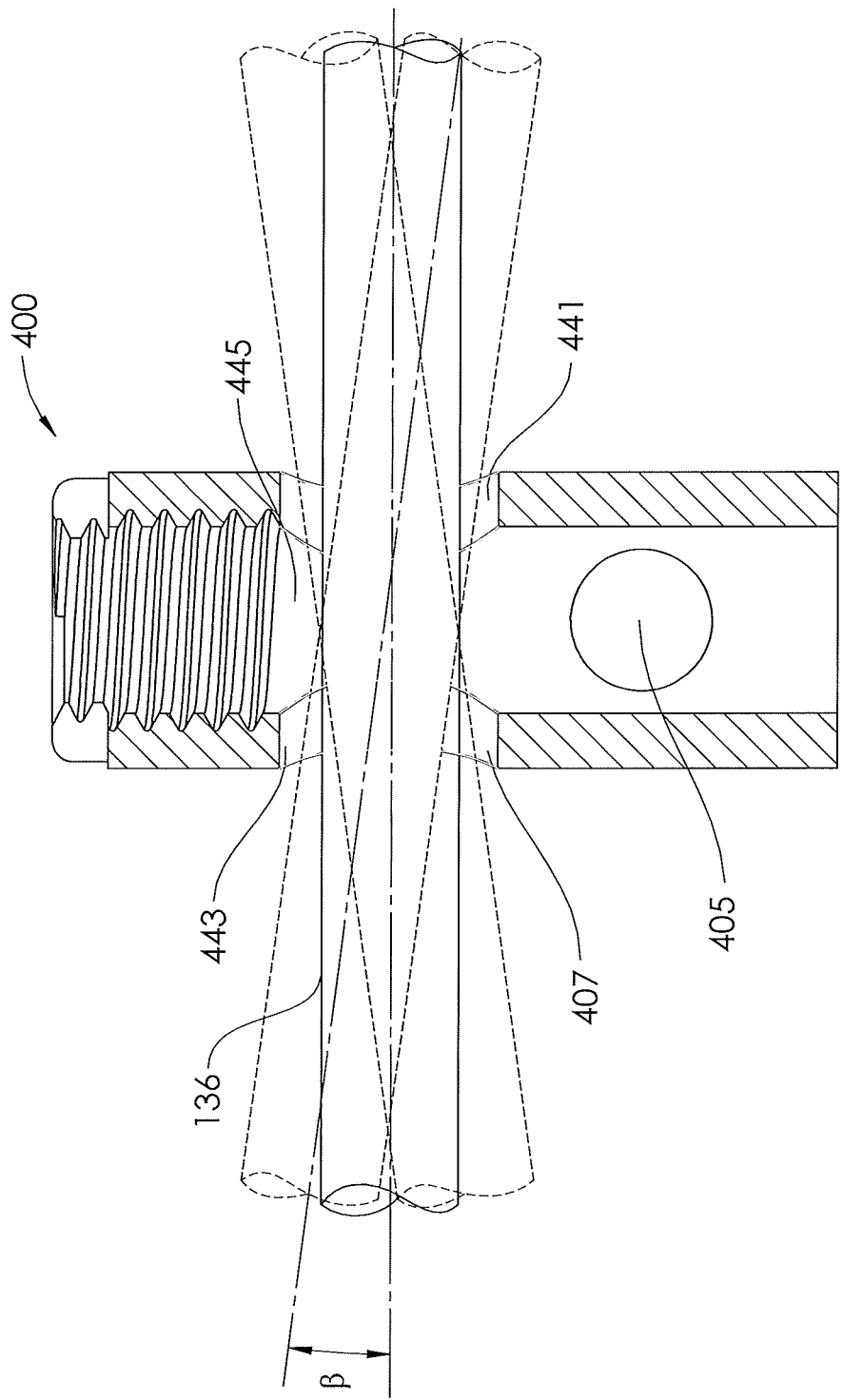
FIG. 22 illustrates a bone screw within a slotted transverse hole of a non-invasively adjustable wedge osteotomy device.

FIG. 22 demonstrates the pivotability of a bone screw in place within a slotted transverse hole (e.g., the second bone screw 136 within the slotted transverse hole 407). The bone screw may pivot through a pivot angle β in either direction (+β, −β). FIGS. 18-20 demonstrate the non-invasively adjustable wedge osteotomy device 400 which is implanted in the tibia 102 being adjusted to increase an angle A of the wedge osteotomy 118. In FIG. 18, the inner shaft 432 extends from the outer housing 430 an initial length D1. The osteotomy 118 is in an initial closed or mostly closed state, and the first bone screw 136 has been secured to the first portion 119 of the tibia 102 so that it is angled at, near, or towards a first extreme of pivot in a first angular direction in relation to the slotted transverse hole 407. More specifically, the head 144 of the first bone screw 136 on the medial side of the first portion 119 is at a lower height in comparison to the distal end 148 on the lateral side of the first portion 119, leaving the first bone screw at an angle −β (see FIG. 22). Though the bone screws in FIGS. 18-20 are shown with short proximal male threads 146, other bone screws may be used, including, for example, lag screws, or fully threaded screws. In FIG. 19, a distraction of the non-invasively adjustable wedge osteotomy device 400 has been performed, causing the inner shaft 432 to extend from the outer housing 430 so that it extends a new length D2, which is greater than the initial length D1. In some embodiments non-invasive distraction may be accomplished by placing the magnetic handpiece 1178 of the external adjustment device 1180 on the skin or clothing in the area of the upper tibia 102 and operating the external adjustment device 1180 to rotate the one or more magnets 1186 which in turn cause the radially-poled permanent magnet 368 (FIGS. 6-7) within the non-invasively adjustable wedge osteotomy device 400 to be magnetically rotated. Extension of the inner shaft 432 out of the outer housing 430 causes the first portion 119 to be lifted away from the second portion 121 thereby opening osteotomy 118 to a wedge angle A2. As osteotomy 118 is opened, the first bone screw 136, which is secured to the first portion 119 of the tibia 102, may be rotated with the first portion 119 (the rotation being allowed/facilitated by the slotted transverse hole 407). In FIG. 19, the first bone screw 136 is shown with a substantially horizontal orientation (i.e., β≈0°). In FIG. 20, additional distraction has been performed (e.g., non-invasive distraction) and the inner shaft 432 has been extended further from the outer housing 430 so that it extends a new, increased length D3. A new, increased wedge angle A3 of the osteotomy results from the additional extension of the inner shaft 432, and the first bone screw 136 has pivoted along with the continued rotation of the first portion 119 of the tibia 102 until the first bone screw 136 is angled at, near, or towards a second extreme of pivot in a second angular direction in relation to the slotted transverse hole 407. More specifically, the head 144 of the first bone screw 136 on the medial side of the first portion 119 is at a higher height in comparison to the distal end 148 on the lateral side of the first portion 119, leaving the first bone screw at an angle +β (see FIG. 22).

Non-invasive distraction while a patient is awake, mobile, and or weight-bearing may allow an optimum wedge angle A to be achieved. In some embodiments, an optimum wedge angle is the wedge angle A at which the patient feels no pain. In other embodiments, an optimum wedge angle is the wedge angle A at which the patient feels no contact of tissue at the knee joint, for example at a medial compartment of the knee joint. In some cases, the wedge angle A may be increased until an anatomical benchmark is reached, for example a Fujisawa overcorrection, which is described further below. Distractions may be done at specific time intervals. For example, the total length of a non-invasively adjustable wedge osteotomy device, as disclosed herein, may be increased about 0.5 mm-1.5 mm per day, or about 0.75 mm-1.25, or any other clinically advantageous rate, until the desired wedge angle is reached. Alternatively, the amount by which a non-invasively adjustable wedge osteotomy device, as disclosed herein, is to be lengthened may be calculated prior to each adjustment procedure (e.g., lengthening, distraction, or adjustment), so that a consistent wedge angle increase (i.e., using trigonometric relationships so that the angle can be increased by a consistent Δβ) is achieved by each adjustment procedure. In some circumstances, any given day's adjustment may be all at once, within a single procedure. Alternatively, any given day's adjustment may be broken up into two or more smaller adjustments or procedures per day (equivalent to the daily desired total). Breaking up adjustments into smaller procedures may advantageously help to minimize pain or discomfort caused by stretching of soft tissue in the knee joint 104. For some patients or in some circumstances it may be desirable to determine the desired rate of device distraction based on a rate of medial cortex increase (the open portion of the osteotomy 118 at the medial edge of the tibia 102). For example, it may desirable to distract the device at a rate sufficient to cause the medial cortex to increase by about 1 mm per day: depending on the width of the tibia 102, among other factors, such a 1 mm daily medial cortex increase may require only between about 0.5 mm and 0.65 mm daily device distraction (i.e., daily increase at the midline). In some cases, once the ultimate desired wedge angle is reached, distraction is stopped, and the wedge osteotomy 118 is allowed to consolidate over a period of time (e.g., days, weeks, or months). The amount of time required for consolidation may depend on the angle of wedge osteotomy 118 increase, the rate of wedge osteotomy increase, whether the patient smokes, whether the patient has diabetes, and the patient's activity level, among other biological factors. During the distraction process (e.g., from implantation to substantial healing), it may be desirable for the patient to place a diminished (i.e., less than normal) amount of force (compression) on the leg being treated, for example, through the use of crutches, braces, wheel chairs, walkers, or the like. Additionally, the patient may be instructed to increase the load placed on the leg during the consolidation phase: compression during consolidation has been positively linked to improved osteogenesis and faster and better healing of the bone.

Figure 21:
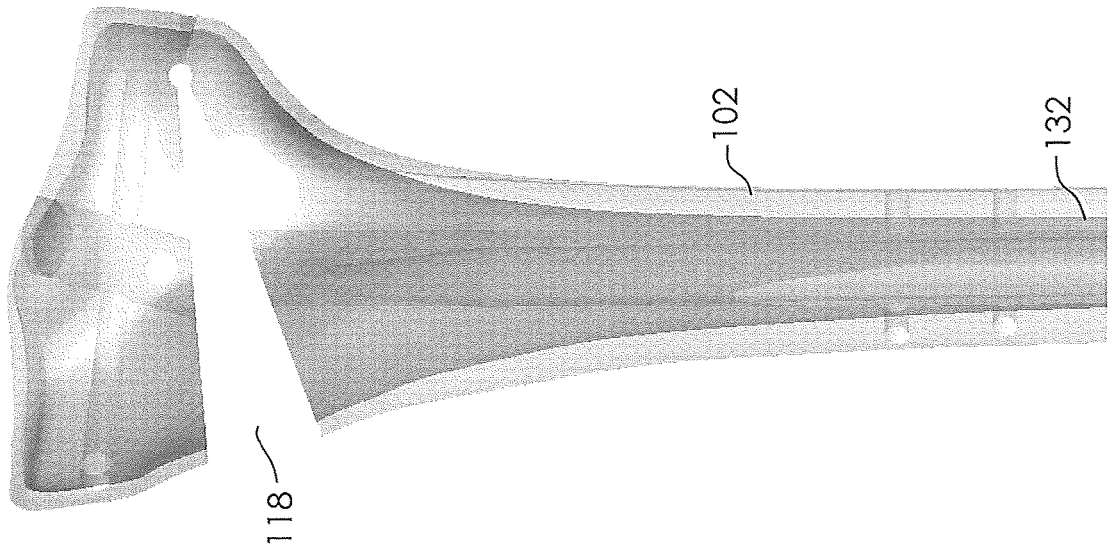
FIG. 21 illustrates a consolidated tibia after removal of a non-invasively adjustable wedge osteotomy device.

In some cases, after the consolidation phase has substantially completed, the devices discloses herein, including the non-invasively adjustable wedge osteotomy device 400 and the bone screws 134, 136, 138, 140, 142 may be removed. A revised tibia 102, after removal of a the non-invasively adjustable wedge osteotomy device, as disclosed herein, is shown in FIG. 21. During the distraction phase and/or the consolidation phase, bone graft may be added to portions of the wedge osteotomy 118 in order to help increase solidification of the tibia 102, for example, between the first portion 119 and the second portion 121.

Figure 30:
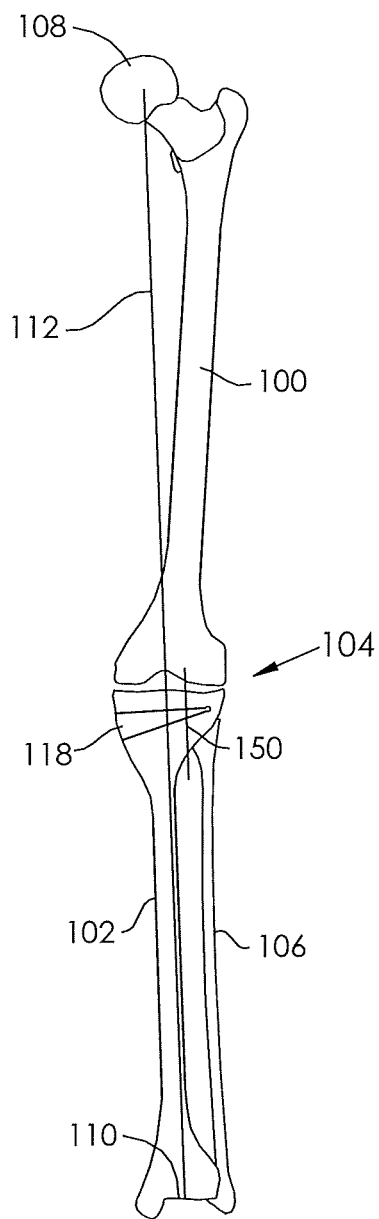
FIG. 30 illustrates a standard correction for the alignment of a knee joint.
Figure 31:
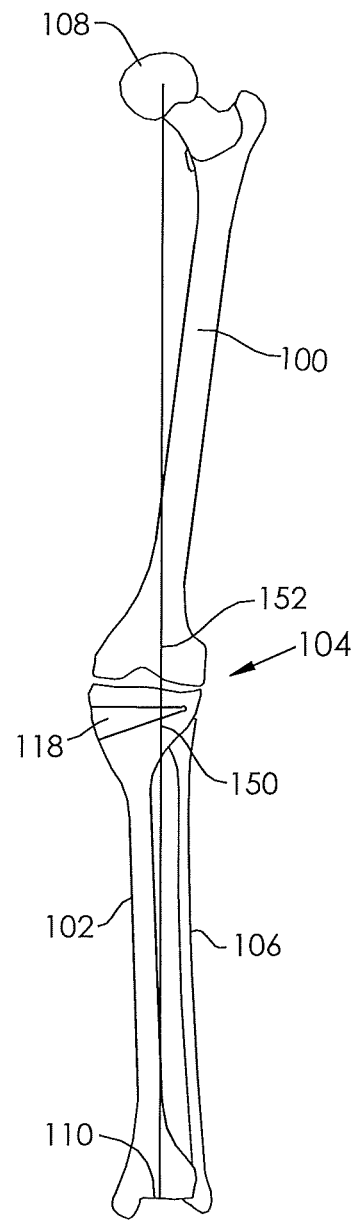
FIG. 31 illustrates a planned overcorrection for the alignment of a knee joint.

FIG. 30 shows the mechanical axis 112 of a tibia 102 that has been adjusted by creating a wedge osteotomy, for example, by using standard methods or the apparatuses and/or methods described herein. The mechanical axis extends from the femur head 108, through the center of the knee joint 104, and to a center point of the ankle joint at the distal tibia 110. Although restoring the mechanical axis 112 through the center of the knee joint 104 has been standard practice in some centers, an alternative method was proposed by Fujisawa (see Fujisawa et al., "The Effect of High Tibial Osteotomy on Osteoarthritis of the Knee: An Arthroscopic Study of 54 Knee Joints", July 1979, Orthopedic Clinics of North America, Volume 10, Number 3, Pages 585-608, the entirety of which is incorporated by reference herein). Fujisawa states that "the ideal correction method is to align the mechanical axis to pass through a point 30 to 40 percent lateral to the midpoint." (Fujisawa et al. at Pages 606-607) An overcorrection axis 150, as taught by Fujisawa, is shown in FIGS. 30-31 and passes through the knee joint 104 at a point that is about 30%-40% lateral of the midpoint in the knee joint 104. As the standard mechanical axis passes through the midpoint in the knee joint 104, the overcorrection axis 150 is about the same percentage lateral to the standard mechanical axis 112. FIG. 31 shows an overcorrection performed by wedge osteotomy of the tibia 102 that reaches approximately the conditions described by Fujisawa. An overcorrected mechanical axis 152 approximates the overcorrection axis 150 through the knee joint 104, extending from the center of the femur head 108 through the knee joint at approximately the overcorrection axis 150, and to the center point of the ankle joint at the distal tibia 110. To achieve overcorrection, the angle of the wedge osteotomy 118 has been increased an additional amount.

Figure 32:
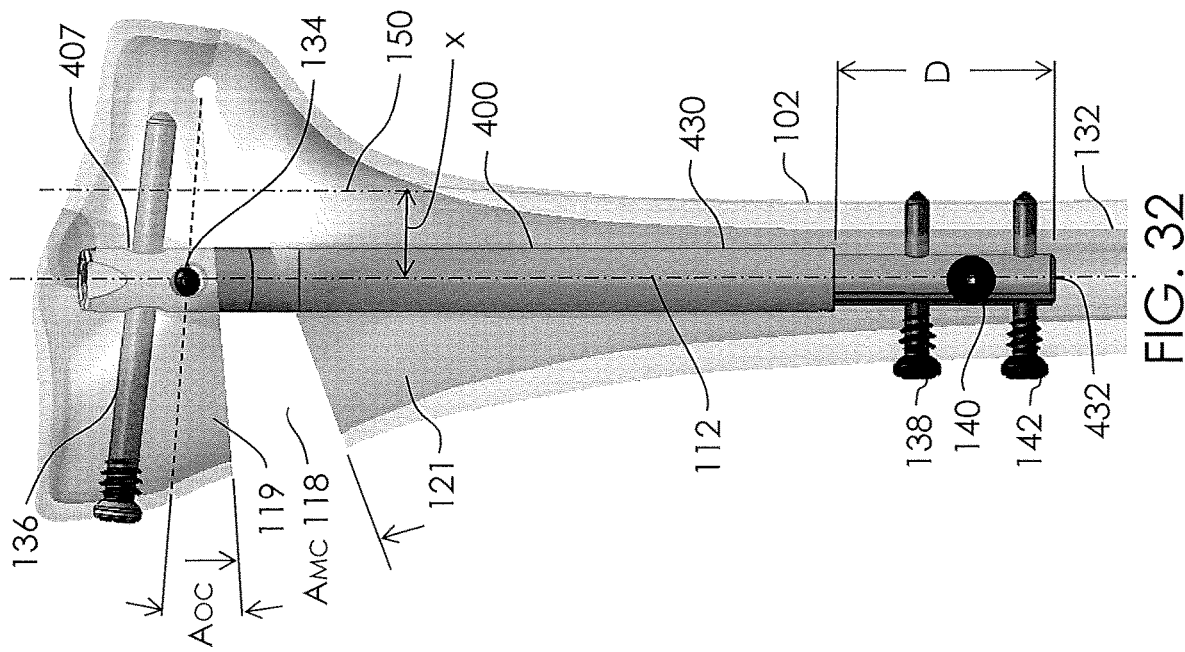
FIG. 32 illustrates a non-invasively adjustable wedge osteotomy device within a tibia in relation to a standard correction axis and a planned overcorrection axis.

FIG. 32 illustrates an embodiment of a non-invasively adjustable wedge osteotomy device, for example the non-invasively adjustable wedge osteotomy device 400, in place within the tibia 102, with the standard mechanical axis 112 and the overcorrection axis 150 indicated. Overcorrection axis 150 is shown a distance x lateral to the standard mechanical axis. In some embodiments, distance x is between about 24%-44%, about 28%-40%, about 30%-38%, and about 32-36% of the total distance from the midline to the lateral extreme. In FIG. 32, the angle of midline correction ("AMC") was performed in order to achieve the mechanical axis 112 as shown. The AMC is defined as the amount of angle of correction required to place the mechanical axis through the center of the knee joint 104, may be up to about 12° or less in many patients, and may be achieved by using non-invasively adjustable wedge osteotomy devices as disclosed herein. In some cases, an angle of greater than 12° is required to achieve a proper overcorrection as described above (e.g., it may be desirable in some patients to achieve an angle of up to about 16°, or even more). Thus, an additional angle of overcorrection ("AOC"), may be needed in order to create the overcorrected mechanical axis 152 as in FIG. 31. In some cases the AOC may be between about 1°-8°, about 2°-7°, about 3°-6°, and about 4°-5°, or the AOC may be any other angle that is physiologically beneficial for the patient. The total resulting correction angle is therefore equal to the sum of angles AMC and AOC.

Another embodiment of a non-invasively adjustable wedge osteotomy device 500, illustrated in FIGS. 23-25, may be configured to allow for an increased amount of angular correction in the tibia 102. The non-invasively adjustable wedge osteotomy device 500 includes an inner shaft 532, which is telescopically distractable from an outer housing 530. In some embodiments, the internal components of the non-invasively adjustable wedge osteotomy device 500 may be similar or identical to those of the other non-invasively adjustable wedge osteotomy devices disclosed herein (for example the non-invasively adjustable wedge osteotomy device 300 of FIGS. 5-6, among others). In some embodiments, a slotted transverse hole 507 extends through the outer housing 530 of the non-invasively adjustable wedge osteotomy device 500. The slotted transverse hole 507 has a generally oblong shape, similar to that described with respect to the embodiments of the non-invasively adjustable wedge osteotomy device shown in FIGS. 10-14. Additionally, the outer housing 530 may have a second slotted hole 586. While the slotted transverse hole 507 may be generally vertically oblong, the second slotted hole 586 may be generally horizontally oblong. The second slotted hole 586 may have a length L and a width W, as shown in FIG. 24. The length L may be configured to be slightly larger than the diameter of a bone screw that is used to secure the non-invasively adjustable wedge osteotomy device 500 to a bone, such that the bone screw is able to pass through the second slotted hole 586. The width W may be chosen such that the bone screw is able to horizontally pivot or angularly displace within the second slotted hole 586. In some embodiments the second slotted hole 586 is configured to be used with a 5 mm bone screw, the length L may be about 5 mm to about 5.2 mm, or about 5.1 mm, and the width W may be about 6 mm to about 9 mm or about 7 mm. In some embodiments, the ratio of width W to length L (i.e., W/L) may be between about 1.08 and about 1.65, or about 1.25 to about 1.54, or about 1.37. The slotted transverse hole 507 and the second slotted hole 586 are located near a first end 568 of the outer housing 530. As shown in FIG. 25, a second end 570 of the outer housing 530 is angled from the first end 568 at a transition point 572. In some embodiments, the angle 578 is between about 2°-18°, about 4°-16°, about 6°-14°, about 8°-12°, and about 10°, or any other angle that is clinically meaningful for any given patient. The second slotted hole 586 may include an anterior opening 588 and a posterior opening 590, which may be oriented in relation to the first end 568 at an angle 576. In some embodiments, the angle 576 is between about 70°-100°, about 75°-95°, about 80°-90°, or about 85°, or any other angle that is clinically meaningful for any given patient. FIG. 23 also illustrates an interface 566 having an internal thread 597, which may be used for releasable detachment of an insertion tool. Similar to what has been described above, the non-invasively adjustable wedge osteotomy device 500 may be inserted by hand or may be attached to an insertion tool (for example a drill guide). In some embodiments, an interface 566 comprising an internal thread 597 is located at or near the first end 568 for reversible engagement with male threads of an insertion tool. Alternatively, such engagement features may be located at or near the inner shaft 532. In other embodiments a tether (e.g., a detachable tether) may be attached to either end of the non-invasively adjustable wedge osteotomy device 500, so that it may be easily removed if placed incorrectly.

Figure 26:
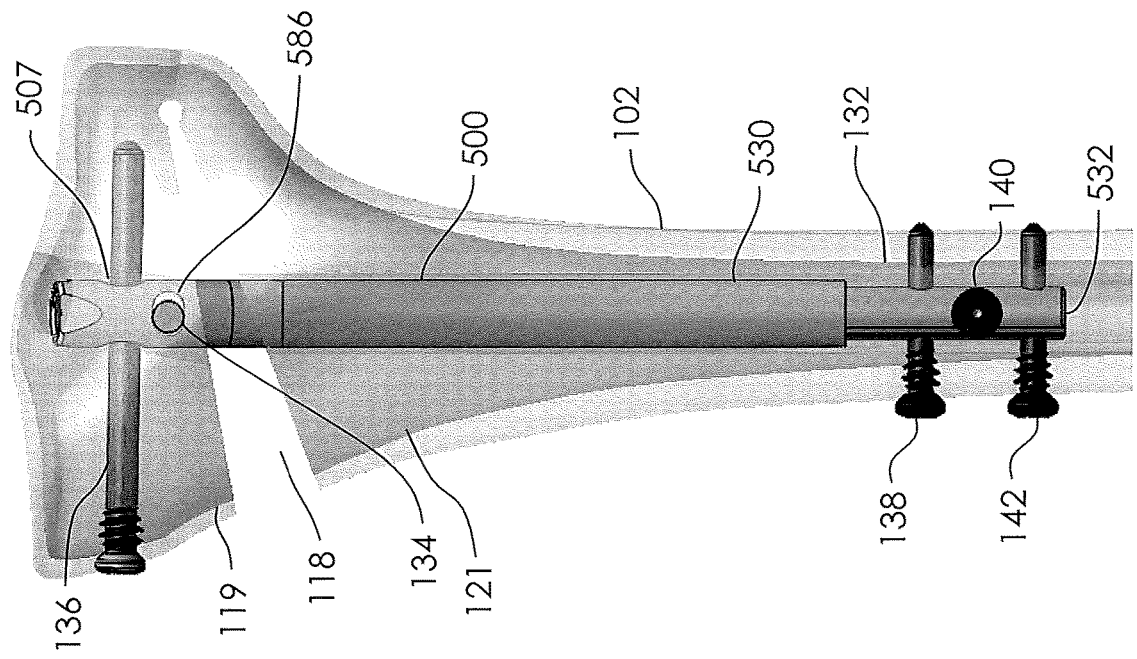
FIG. 26 illustrates the non-invasively adjustable wedge osteotomy device of FIG. 23 within a tibia in a substantially non-adjusted state.
Figure 27:
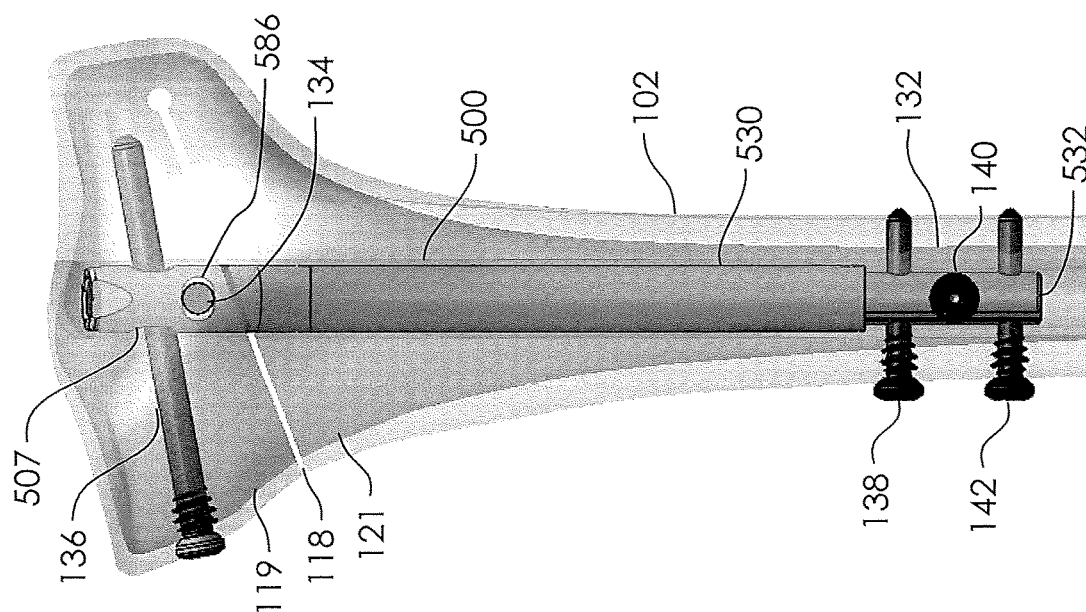

FIGS. 26-29 illustrate how the second slotted hole 586 of the non-invasively adjustable wedge osteotomy device 500 works in conjunction with the slotted transverse hole 507 to advantageously facilitate the possibility of an increased amount of angular correction between a first portion 119 and second portion 121 of the tibia 102. First bone screw 134 is illustrated without a head merely so the shaft of the first bone screw 134 is visible within the second slotted hole 586. In FIG. 26, the osteotomy 118 is substantially closed and the inner shaft 532 has not been significantly distracted from the outer housing 530. The first bone screw 134 may (at least initially) preferably be centrally oriented with respect to the width W of the second slotted hole 586. In FIG. 27, the inner shaft 532 has been distracted further out of the outer housing 530. As the outer housing 530 moves, it pushes up on the first bone screw 134 and the second bone screw 136, which in turn push upward on the first portion of the tibia 102, causing the first portion of the tibia 119 to pivot about the hinge. As the first portion of the tibia pivots, the second bone screw 136 pivots within the slotted transverse hole 507, as described with respect to other embodiments disclosed herein, such as the non-invasively adjustable wedge osteotomy device 400. While the second bone screw 136 pivots, the first bone screw 134 may slide medially (i.e., towards the left side of FIG. 27). In FIG. 28, the inner shaft 532 has been distracted still further out of the outer housing 530. As the second bone screw 136 pivots even further within the slotted transverse hole 507, the first bone screw 134 may be forced back towards a central location with respect to the width W of the second slotted hole 586. In FIG. 29, the inner shaft 532 is distracted still further out of the outer housing 530, and, as the second bone screw 136 pivots still further within the slotted transverse hole 507, the first bone screw 134 may slide laterally (i.e., towards the right side of FIG. 27). The elongated orientation of the second slotted hole 586 along the width W, may advantageously add additional freedom to the movement of the non-invasively adjustable wedge osteotomy device 500 as it distracts the first portion 119 from the second portion 121 of the tibia 102, and allow for an increased amount of angulation, for example, a total of between about 10°-22°, about 12°-20°, about 14°-18°, or about 16°, or any other degree of angulation that is clinically meaningful for any given patient. Devices (e.g., other non-invasively or invasively adjustable wedge osteotomy devices, including those disclosed herein) that do not have both the slotted transverse hole 507 and second slotted hole 586, may be able to achieve about 16° of angulation. However, for such devices to do so may cause axial lengthening between the first portion 119 and the second portion 121 of the tibia 102, as opposed to merely changing the angle between the first portion 119 and the second portion 121. Axial lengthening between the first portion 119 and the second portion 121 of the tibia may cause unneeded and deleterious stresses on and/or even fracture of the hinge 450 formed by the connection between the first portion 119 and the second portion 121 of the tibia 102 (shown in FIG. 15). Were the first portion 119 to fracture from the second portion 121 and away from the rest of the tibia 102, the first portion 119 could be axially or nonangularly distracted away from the second portion 121, and would not correct the angle of the knee joint 104. Therefore, incorporation of both the slotted transverse hole 507 and second slotted hole 586 into the non-invasively adjustable wedge osteotomy device 500 may allow a full 16° of angulation (or more) with little to no axial elongation, which can be advantageously achieved without significant damage to the hinge 450. In some cases, angulation of up to 25° may be possible while still maintaining the same anterior to posterior slope on the top surface of the tibia 102.

Figure 33:
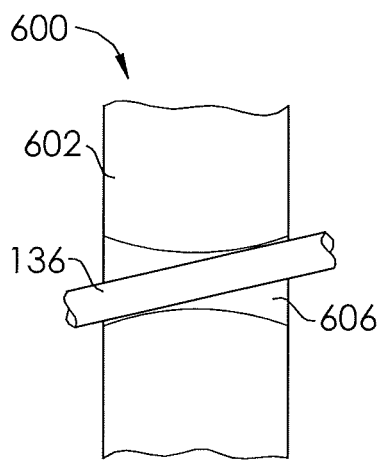
FIGS. 33-34 illustrate a tapered or hourglass shaped anchor hole of a non-invasively adjustable wedge osteotomy device with an anchor in various positions.
Figure 34:
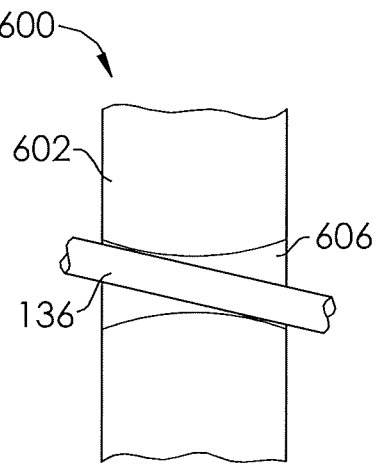

In some embodiments, an alternative to the slotted transverse hole 407, 507 may be used. FIGS. 33-34 illustrate an hourglass shaped hole for enabling pivoting of a bone screw. Wall 602 (for example, of non-invasively adjustable wedge osteotomy device 600) may have a tapered or hourglass-shaped hole 606 passing through the wall 602. The tapered or hourglass-shaped hole 606 may have a circular cross-section that varies in diameter along its length. As the wedge osteotomy device distracts/retracts, as disclosed herein, the second bone screw 136 is allowed to pivot, for example, from the position in FIG. 33 to the position in FIG. 34. The degree of pivot is directly dependent on the variance in diameter: the larger the outer diameter, the more pivot is allowed. It is contemplated that embodiments of the tapered or hourglass-shaped hole 606 may permit pivot angles (i.e., the degree of maximum pivot to maximum pivot, such as the angular difference between the second bone screw 136 shown in FIG. 33 to the second bone screw 136 shown in FIG. 34) of between about 5°-40°, about 10°-35°, about 15°-30°, and about 20°-25°, or any other angle that is clinically meaningful for any given patient.

Figure 35:
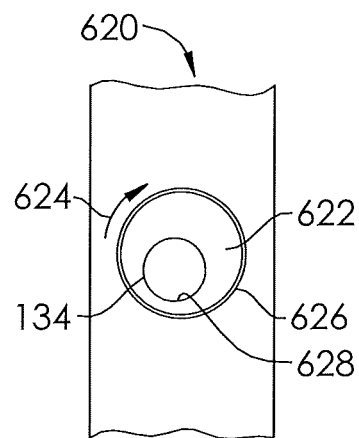
FIGS. 35-37 illustrate a non-invasively adjustable wedge osteotomy device having an eccentric bearing in various positions.
Figure 36:
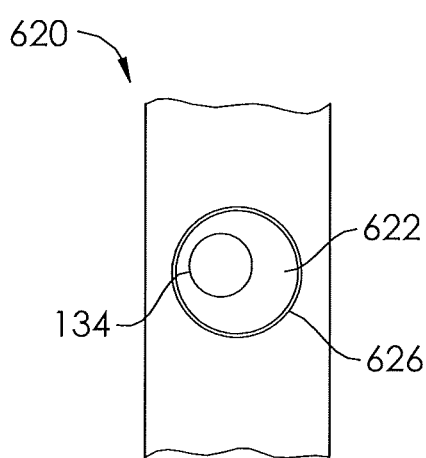
Figure 37:
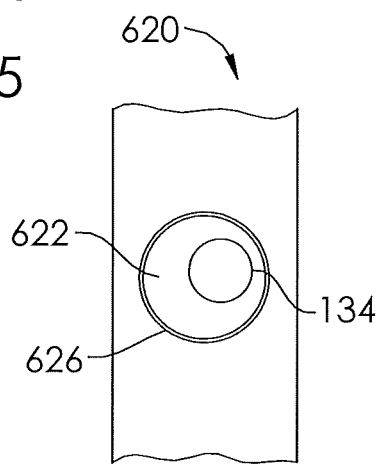

In some embodiments, other alternatives to the second slotted hole 586, as illustrated in FIGS. 35-37, may be used. FIGS. 35-37 illustrate an eccentric bearing type hole for enabling pivoting of a bone screw. For example, hole 626 may be incorporated into the wall of a non-invasively adjustable wedge osteotomy device as is disclosed herein, such as non-invasively adjustable wedge osteotomy device 620. In some embodiments, the hole 626 is configured to extend in a generally anterior to posterior/posterior to anterior orientation when the non-invasively adjustable wedge osteotomy device 620 is implanted in the tibia 102. In other embodiments, the hole 626 is configured to extend in a generally medial to lateral/lateral to medial orientation when the non-invasively adjustable wedge osteotomy device 620 is implanted in the tibia 102. In yet other embodiments, the hole 626 extends through the non-invasively adjustable wedge osteotomy device 620 at an angle between medial to lateral, and anterior to posterior. In some embodiments, the hole 626 may extend through the non-invasively adjustable wedge osteotomy device 620 at an angle substantially perpendicular to the longitudinal axis of the non-invasively adjustable wedge osteotomy device 620. In other embodiments, the hole 626 may extend through the non-invasively adjustable wedge osteotomy device 620 at an angle not perpendicular to the longitudinal axis of the non-invasively adjustable wedge osteotomy device 620, for example about 1°-30° off perpendicular, about 2°-25° off perpendicular, about 3°-20° off perpendicular, about 4°-15° off perpendicular, or about 5°-10° off perpendicular, or any other angle off perpendicular that is clinically meaningful to any given patient. An eccentric bearing 622 may be rotationally held within the hole 626. The eccentric bearing 622 may be made from a lubricious material (e.g., PEEK, UHMWPE, etc.) so as to advantageously decrease friction in the system. The eccentric bearing 622 has an off-center hole 628 through which an object may be placed (e.g., the first bone screw 134). When distracting a non-invasively adjustable wedge osteotomy device 620 incorporating an eccentric bearing 622 as shown in FIGS. 35-37, the off-center hole 628 (and thus any object extending through the off-center hole 628, such as the first bone screw 134) rotates in relation to the hole 626, for example, in a first rotational direction 624. FIG. 35 shows a location of approximately seven o'clock; FIG. 36 shows a location of approximately ten o'clock; and FIG. 37 shows a location of approximately two o'clock. The eccentric bearing 622 may be fixedly held within the hole 626 of the non-invasively adjustable wedge osteotomy device 620, for example with snaps, detents, welds, glues, epoxies, or any other means of fixation appropriate for the application. Alternatively, the eccentric bearing 622 may be inserted into the hole 626 by a user. The motion of the first bone screw 134 within the eccentric bearing 622 may have characteristics similar to motion of the first bone screw 134 within the second slotted hole 586 (discussed with respect to FIGS. 26-29), though the eccentric bearing 622 may allow some additional movement of an object extending through the off-center hole with respect to the non-invasively adjustable wedge osteotomy device 620, for example vertical (i.e., up and down) movement of an object extending through the off-center hole 628 in addition to the lateral (i.e., left and right) movement of an object extending through the off-center hole 628.

Figure 38:
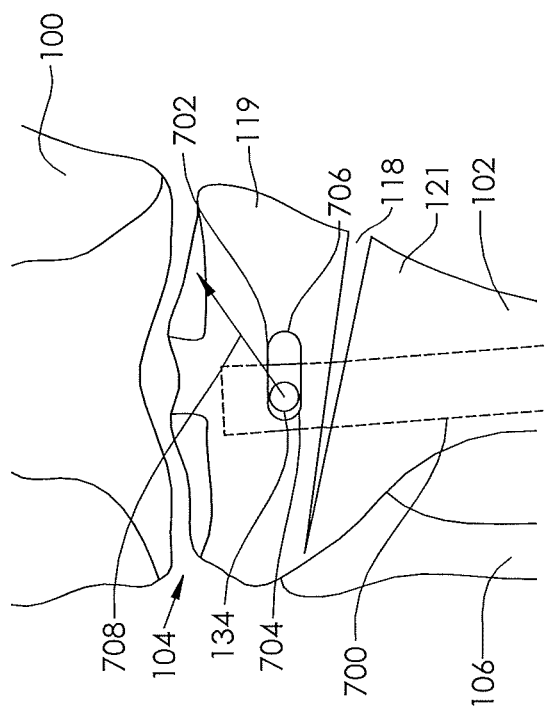

In FIG. 38, an elongated hole 702 has been cut or drilled into the upper portion 119 of the tibia 102 in a substantially horizontal fashion. The elongated hole 702 has a first end 704 (shown here laterally) and a second end 706 (shown here medially). A non-invasively adjustable wedge osteotomy device 700, as shown in FIG. 40, may be placed within a drilled or reamed medullary canal within the tibia 102, and a first bone screw 734 inserted through an anchor hole 716 in the non-invasively adjustable wedge osteotomy device 700. In some embodiments, the anchor hole 716 has an internal threaded portion 722 configured to engage a male thread 710 of the first bone screw. The first bone screw 734 has a head 718 and a distal end 720. The elongated hole 702 (shown in FIGS. 38-40) is drilled through the first cortex 712 and the second cortex 714. The distal end 720 of the first bone screw may then be inserted through the elongated hole 702. In some embodiments, including the embodiment shown in FIG. 40, the male thread 710 engages with the first cortex 712 thereby cutting partial threads in the bone of the first cortex 712 and allowing the male thread 710 to pass through the first cortex 712. Once the male thread 710 has passed through the first cortex 712, it may be threaded into the internal threaded portion 722 of the anchor hole 712, thereby fixing/locking/securing the bone screw 734 to the to the non-invasively adjustable wedge osteotomy device 700. Because the bone screw 734 is only threaded in the middle (i.e., has a smooth neck, and smooth distal end), it may slide or displace along the elongated hole 702 in the upper portion 119 of the tibia 102 from the first end 704 to the second end 706, all while the middle threaded portion remains secured to the non-invasively adjustable wedge osteotomy device 700.

Figure 39:
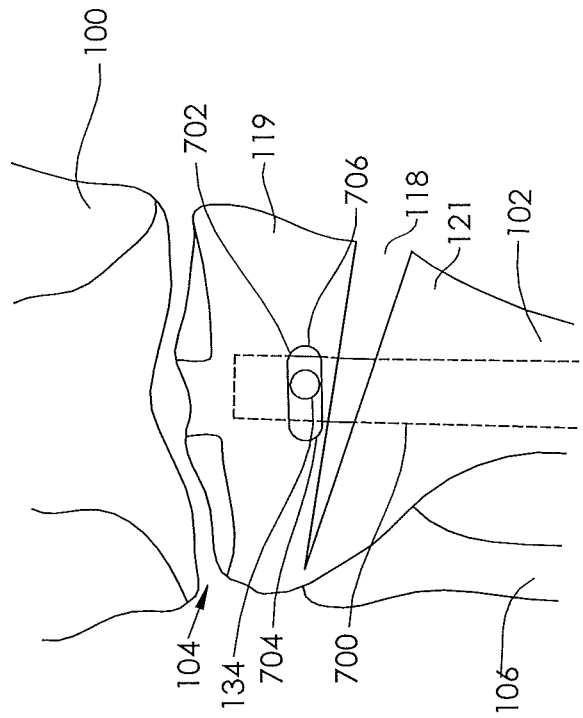
FIGS. 38-39 illustrate a knee joint with a non-invasively adjustable wedge osteotomy device implanted in a tibia in various states of distraction.
Figure 40:
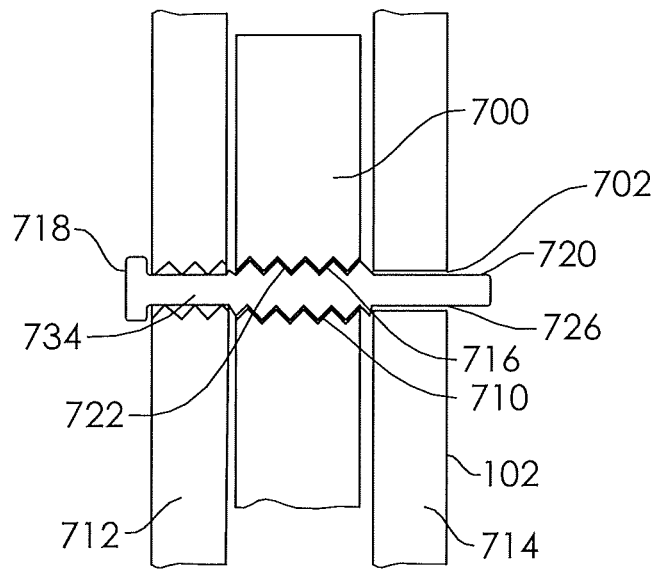
FIG. 40 illustrates an internally threaded anchor hole of an embodiment of the non-invasively adjustable wedge osteotomy device of FIG. 38.

As the non-invasively adjustable wedge osteotomy device 700 is distracted, the first bone screw 134, 734 is able to follow a path 708 (shown in FIG. 38) while the angle of the osteotomy 118 increases and as the first bone screw 134, 734 moves away from the first end 704 of the elongated hole 702 and towards the second end 706 of the elongated hole 702, as shown in FIGS. 38 and 39. In some embodiments, the first bone screw 134 may be replaced by a pin that inserts through an anchor hole in the non-invasively adjustable wedge osteotomy device 700. Such a pin may be anchored using a close fit, friction fit, snap fit, spring fit, or the like.

Figure 41:
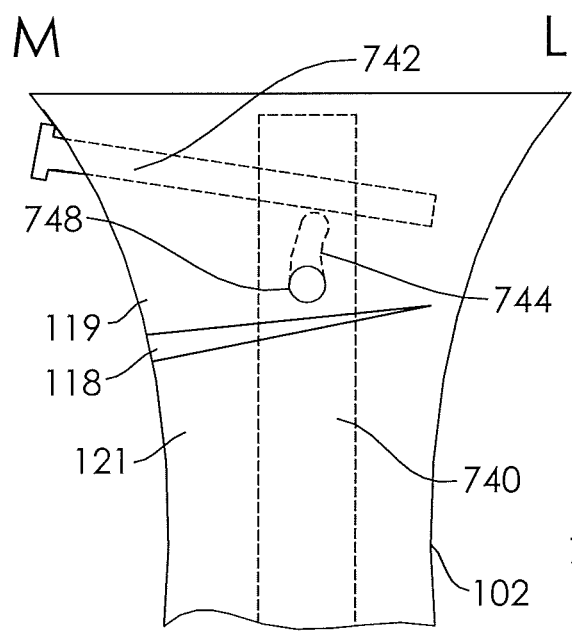
FIG. 41 illustrates a front view of a tibia implanted with an embodiment of a non-invasively adjustable wedge osteotomy device.
Figure 42:
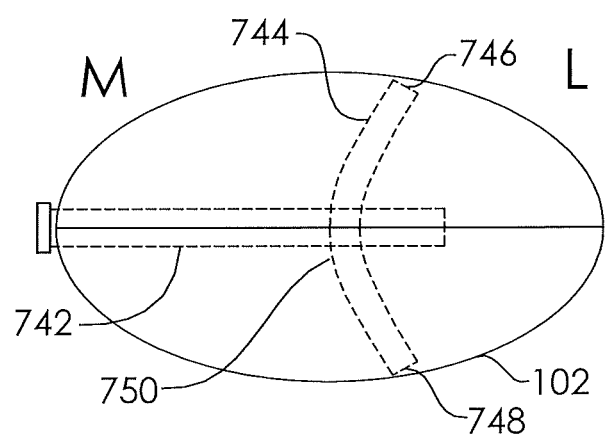
FIG. 42 illustrates a top view of the tibia of FIG. 41.

FIGS. 41-42 illustrate an embodiment of a non-invasively adjustable wedge osteotomy device 740 which has been implanted and secured to an upper portion 119 of the tibia 102. Among many other elements, that may be interchangeable with this disclosed elsewhere in this application, the non-invasively adjustable wedge osteotomy device 740 includes a curved anterior-posterior pin 744 and a bone screw 742. The non-invasively adjustable wedge osteotomy device 740 may be configured, as described herein with respect to other embodiments, to allow the bone screw 742 to pivot, displace, slide, or otherwise move during distraction or retraction of the non-invasively adjustable wedge osteotomy device 740. In some embodiments, the curved anterior-posterior pin 744 has a curved central portion 750 that can be inserted through a hole (such as an anchor hole) of the non-invasively adjustable wedge osteotomy device 740, a first straight end 746 and a second straight end 748.

To insert the curved anterior-posterior pin 744, a hole may be drilled in each of the cortices (anterior to posterior/posterior to anterior) of the upper portion 119 of the tibia 102. The curved anterior-posterior pin 744 may be inserted into the hole in the first side of the first portion 119, through the non-invasively adjustable wedge osteotomy device 740, and out of the hole in the second side of the first portion 119. Thereby, the curved anterior-posterior pin 744 may rotationally engage the first portion 119 and the non-invasively adjustable wedge osteotomy device 740 by using the first straight end 746 and the second straight end 748. When the non-invasively adjustable wedge osteotomy device 740 is distracted, the curved anterior-posterior pin 744 may advantageously rotate within the holes (about the first straight end 746 and the second straight end 748), thereby allowing the anchor hole of the non-invasively adjustable wedge osteotomy device 740 to move in a lateral or medial direction and facilitate displacement in multiple axes simultaneously, as described with respect to other embodiments herein.

Figure 44:
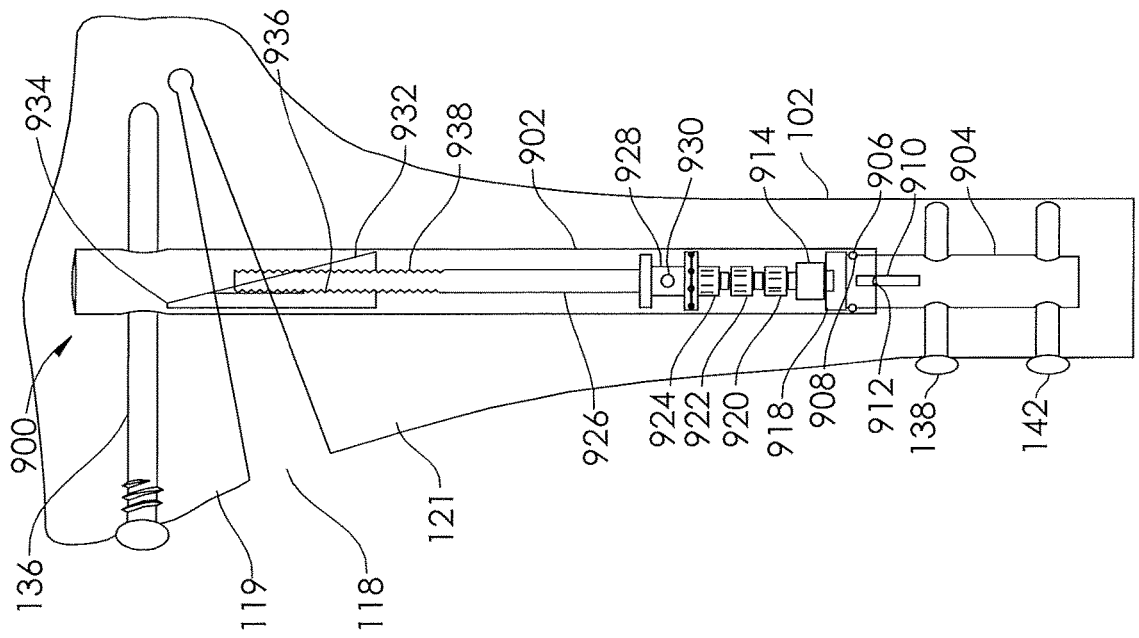
FIGS. 43-44 illustrate a front view of a tibia implanted with another embodiment of a non-invasively adjustable wedge osteotomy device in various states of distraction.
Figure 43:
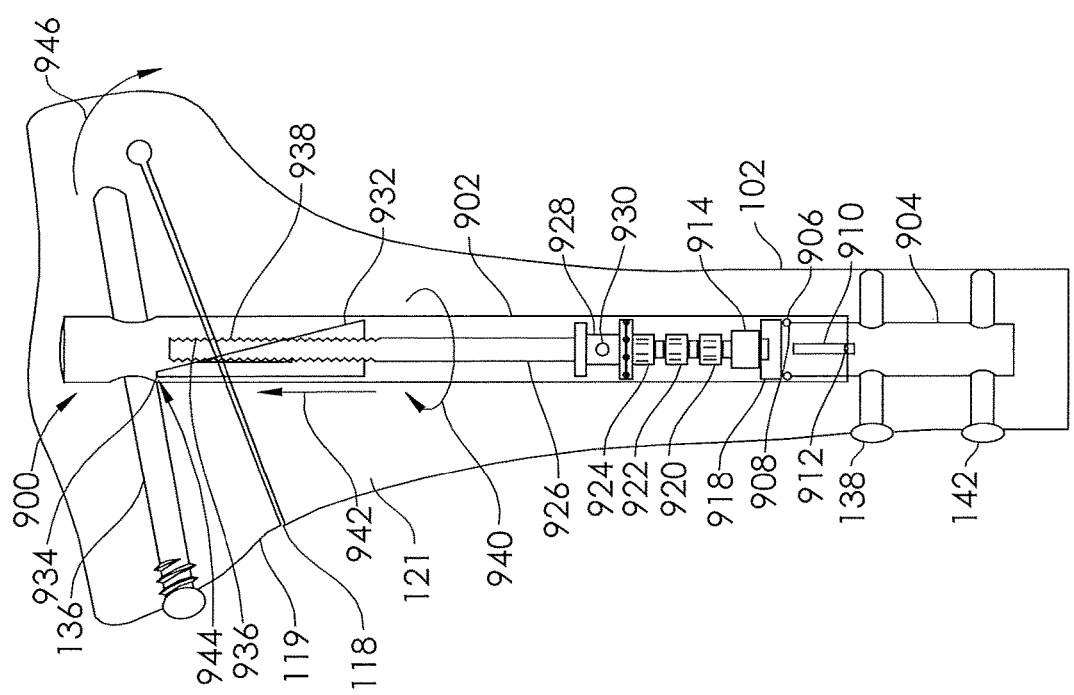

FIGS. 43-44 illustrate an embodiment of a non-invasively adjustable wedge osteotomy device 900 implanted within a tibia 102. The non-invasively adjustable wedge osteotomy device 900 comprises an outer housing 902 and an inner shaft 904, telescopically located within the outer housing 902. FIGS. 43-44 illustrate two distal bone screws 138, 142. But, it should be understood that any number of bone screws may be used. In the same way, FIGS. 43-44 illustrate only a single proximal bone screw 136. Again, it should be understood that this is for illustration purposes only and that more than one bone screw (e.g., 2 bone screws) may be used to anchor the non-invasively adjustable wedge osteotomy device 900 to the first portion 119 of the tibia 102. A second proximal bone screw (similar to the bone screw 134 of FIGS. 15-20) may be incorporated and may provide the advantageous benefit of rotationally stabilizing the upper portion 119 and lower portion 121 of the tibia 102 in relation to the longitudinal axis of the tibia 102.

In some embodiments, the rotational orientation between the outer housing 902 and inner shaft 904 is maintained by a longitudinal groove 910 on the outer surface of the inner shaft 904 and a radial projection 912 extending from the inner surface of the outer housing 902 and configured to slide within the longitudinal groove 910. During actuation, rotation of screw 136 may pull on the outer housing 902 at larger angles; consequently, the outer housing 902 and inner shaft 904 may advantageously be able to longitudinally translate in relation to each other. The inner contents of the non-invasively adjustable wedge osteotomy device may advantageously be protected from the harsh environment within the body. For example, an o-ring seal 906 may be contained within a circumferential groove 908 in the inner portion of the outer housing 902 to provide a dynamic seal between the outer housing 902 and the inner shaft 904.

In some embodiments, a magnet 914 is rotationally carried by the end of the inner shaft 904 via a radial bearing 918. The magnet 914 may be carried within a rotatable magnet housing (not shown). Gear stages 920, 922, 924 couple the magnet 914 to a lead screw 926. The lead screw 926 is coupled non-rigidly to the output of the final gear stage (i.e., gear stage 924) (e.g., by a coupler 928), and may be held in place by a pin 930. The magnet 914 may be rotated by an external moving magnetic field, thereby causing rotation of the lead screw 926. Step-down gear ratios may be used so that several rotations of the magnet 914 are necessary to cause one rotation of the lead screw 926. Additional description and examples of gears stages, such as planetary gear stages, that may be used are included above. In some embodiments, gear stages are not included, leaving a 1:1 ratio (i.e., one rotation of the magnet 914 causes one rotation of the lead screw 926. The rotation of the lead screw 926 causes longitudinal movement of a nut 932, which may have a distal fulcrum 934. An inner thread 936 of the nut 932 threadingly engages an outer thread 938 of the lead screw 926. Rotation of the lead screw 926 in a first rotational direction 940 causes movement of the nut 932 in a first longitudinal direction 942, forcing the distal fulcrum 934 against the bone screw 136 at contact location 944, causing the bone screw 136 and the upper portion 119 of the tibia 102 to generally follow a curved path 946, generally around the contact location 944. In some embodiments, some sliding between the bone screw 136 and the distal fulcrum 934 may occur (that is to say that the distal fulcrum 934 is not a pure fulcrum, which is fixed at a single point with no sliding). The wedge osteotomy 118 is thus caused to open, as shown in FIG. 44. In some embodiments, adjustment of the non-invasively adjustable wedge osteotomy device 900 does not directly cause longitudinal movement of the outer housing 902 with respect to the inner shaft 904 (as has been disclosed with certain other embodiment). Instead, the outer housing 902 and inner shaft 904 may passively move longitudinally with respect to each other, to accommodate length change that may occur as a result of the pivoting of the bone screw 136 and the upper portion 119 of the tibia 102 during the adjustment (for example from the condition in FIG. 43 to the condition in FIG. 44).

Figures 45, 46:
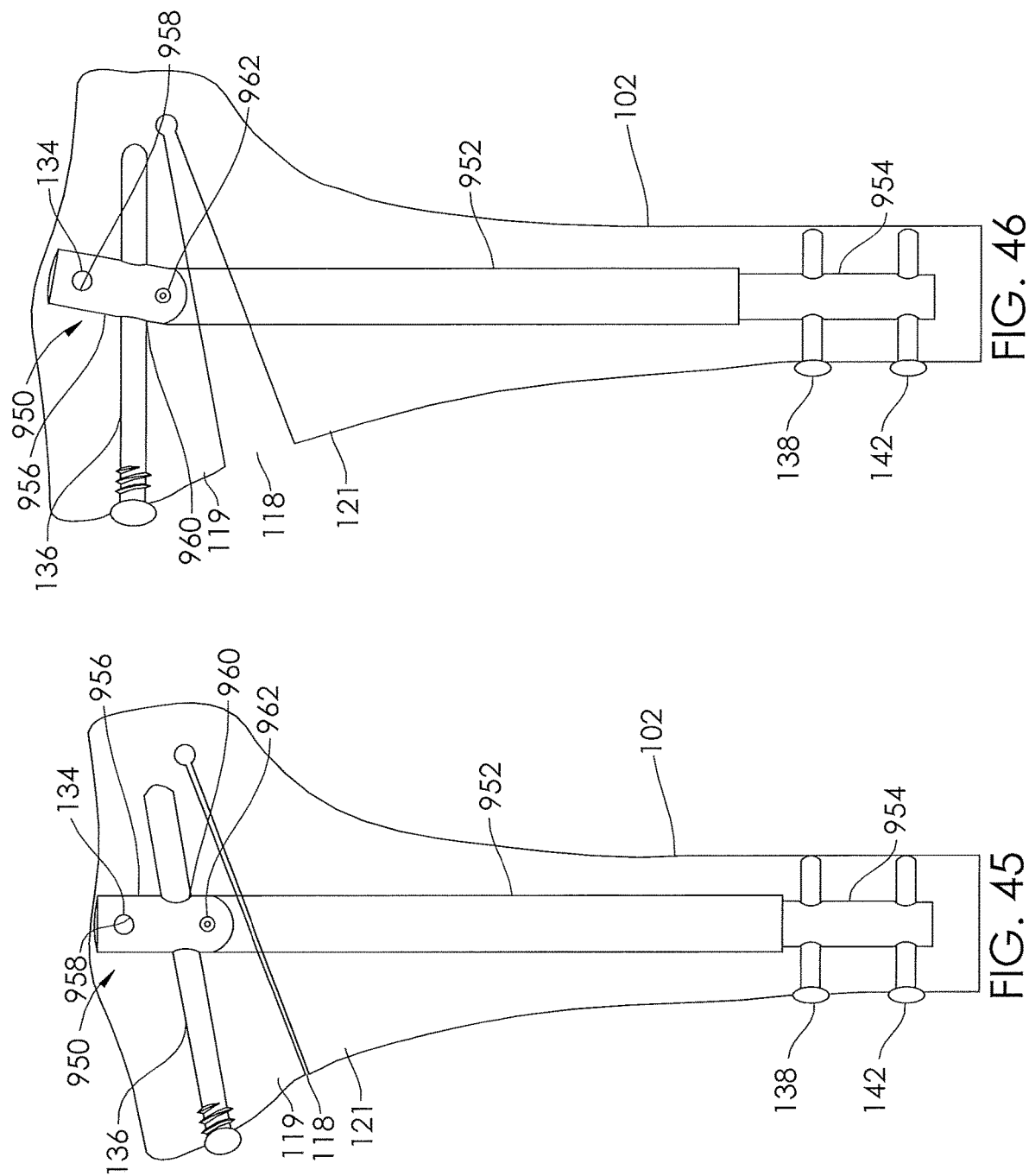
FIGS. 45-46 illustrate a front view of a tibia implanted with another embodiment of a non-invasively adjustable wedge osteotomy device in various states of distraction.

FIGS. 45-46 illustrate an embodiment of a non-invasively adjustable wedge osteotomy device 950 implanted within a tibia 102. The non-invasively adjustable wedge osteotomy device 950 includes an outer housing 952 and an inner shaft 954, which is telescopically located within the outer housing 952. FIGS. 45-46 illustrate two distal bone screws 138, 142. But it should be understood that any number of bone screws may be used. A first bone screw 134 is used to secure a pivoting member 956 to the upper portion 119 of the tibia 102. The first bone screw 134 passes through an anchor hole 958. In some embodiments, the anchor hole 958 is configured to allow rotation between the first bone screw 134 and the anchor hole 958 of the pivoting member 956. An angled anchor hole 960 through the pivoting member 956 allows the passage of a second bone screw 136. The angled anchor hole 960 may have a diameter only just larger than the diameter of the bone screw 136. Therefore, when the bone screw 136 is inserted through the angled anchor hole 960, it is held substantially fixed with respect to the pivoting member 956 (i.e., the angled anchor hole 960 does not allow the second bone screw 136 to pivot or rock substantially in relation to the pivoting member 956). The pivoting member 956 may be coupled to the outer housing 952 by a pivot joint 962. The internal components of the non-invasively adjustable wedge osteotomy device 950 may be similar to those described herein with respect to other embodiments, including those shown in FIGS. 5-7.

FIG. 45 shows the non-invasively adjustable wedge osteotomy device 950 in a substantially undistracted condition whereas FIG. 46 shows the non-invasively adjustable wedge osteotomy device 950 in a distracted condition. As the inner shaft 954 is distracted from the outer housing 952, the pivoting member 956, the upper portion 119 of the tibia 102 and the second bone screw 136 pivot—the second bone screw and the pivoting member 956 pivot about the pivot joint 962 in relation to the outer housing 952 and the lower portion 121 of the tibia 102, thus causing the wedge osteotomy 118 to angularly open and the upper portion 119 of the tibia 102 to pivot about the joint/hinge. In some embodiments, the pivoting member 956 may be pivotably coupled to the inner shaft 954, instead of the outer housing 952. In some embodiments, the pivotable joint 962 may be replaced by a ball joint, which allows additional degrees of freedom between the pivoting member 956 and the outer housing 952.

Throughout the embodiments presented, a radially-poled permanent magnet (e.g. 368 of FIG. 6) is used as a noninvasively-actuatable driving element to generate movement in a non-invasively adjustable wedge osteotomy device. FIGS. 47-50 schematically show four alternate embodiments, in which other types of energy transfer are used in place of permanent magnets.

Figure 47:
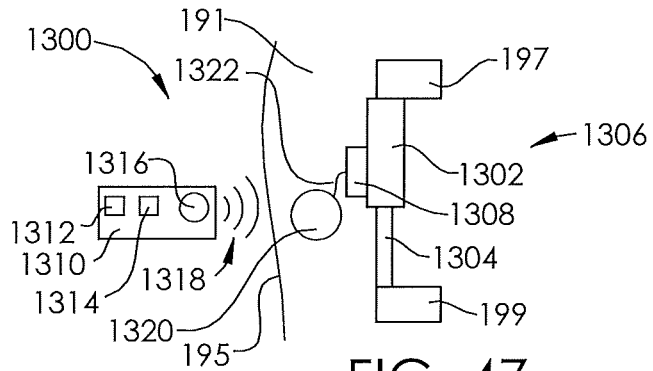
FIGS. 47-50 schematically illustrate various embodiments of a driving element of a non-invasively adjustable wedge osteotomy device.

FIG. 47 illustrates an embodiment of a non-invasively adjustable wedge osteotomy system 1300 including an implant 1306 having a first implant portion 1302 and a second implant portion 1304, the second implant portion 1304 non-invasively displaceable with relation to the first implant portion 1302. The first implant portion 1302 is secured to a first portion of the body 197 and the second implant portion 1304 is secured to a second portion of the body 199 within a patient 191. A motor 1308 is operable to cause the first implant portion 1302 and the second implant portion 1304 to displace relative to one another. In some embodiments, an external adjustment device 1310 has a control panel 1312 for input by an operator, a display 1314, and a transmitter 1316. The transmitter 1316 sends a control signal 1318 through the skin 195 of the patient 191 to an implanted receiver 1320. Implanted receiver 1320 may communicate with the motor 1308 via a conductor 1322. The motor 1308 may be powered by an implantable power source (e.g., a battery), or may be powered or charged by inductive coupling.

Figure 48:
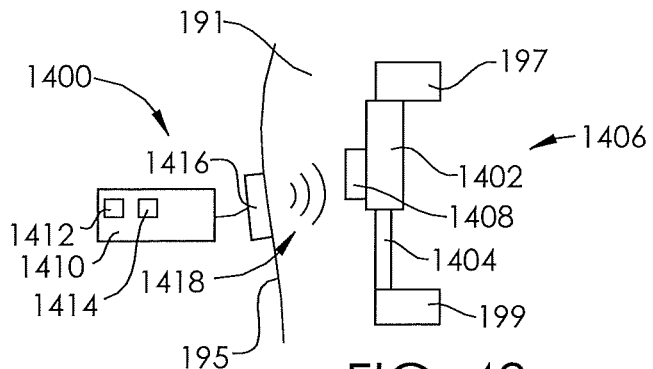

FIG. 48 illustrates an embodiment of a non-invasively adjustable wedge osteotomy system 1400 including an implant 1406 having a first implant portion 1402 and a second implant portion 1404, the second implant portion 1404 non-invasively displaceable with relation to the first implant portion 1402. The first implant portion 1402 is secured to a first portion of the body 197 and the second implant portion 1404 is secured to a second portion of the body 199 within a patient 191. An ultrasonic motor 1408 is operable to cause the first implant portion 1402 and the second implant portion 1404 to displace relative to one another. In some embodiments, an external adjustment device 1410 has a control panel 1412 for input by an operator, a display 1414, and an ultrasonic transducer 1416 that is coupled to the skin 195 of the patient 191. The ultrasonic transducer 1416 produces ultrasonic waves 1418 which pass through the skin 195 of the patient 191 and operate the ultrasonic motor 1408.

Figure 49:
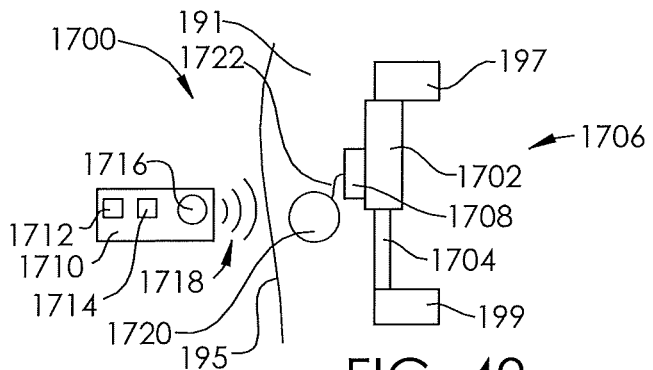

FIG. 49 illustrates an embodiment of a non-invasively adjustable wedge osteotomy system 1700 comprising an implant 1706 having a first implant portion 1702 and a second implant portion 1704, the second implant portion 1704 non-invasively displaceable with relation to the first implant portion 1702. The first implant portion 1702 is secured to a first portion of the body 197 and the second implant portion 1704 is secured to a second portion of the body 199 within a patient 191. A shape memory actuator 1708 is operable to cause the first implant portion 1702 and the second implant portion 1704 to displace relative to one another. In some embodiments, an external adjustment device 1710 has a control panel 1712 for input by an operator, a display, 1714 and a transmitter 1716. The transmitter 1716 sends a control signal 1718 through the skin 195 of the patient 191 to an implanted receiver 1720. Implanted receiver 1720 may communicate with the shape memory actuator 1708 via a conductor 1722. The shape memory actuator 1708 may be powered by an implantable power source (e.g., a battery), or may be powered or charged by inductive coupling.

Figure 50:
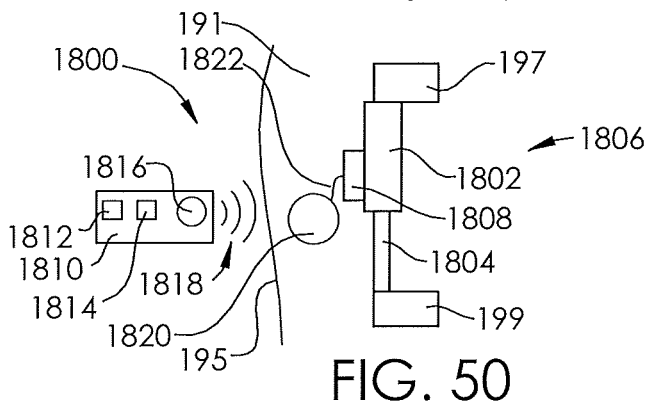

FIG. 50 illustrates an embodiment of a non-invasively adjustable wedge osteotomy system 1800 including an implant 1806 having a first implant portion 1802 and a second implant portion 1804, the second implant portion 1804 non-invasively displaceable with relation to the first implant portion 1802. The first implant portion 1802 is secured to a first portion of the body 197 and the second implant portion 1804 is secured to a second portion of the body 199 within a patient 191. A hydraulic pump 1808 is operable to cause the first implant portion 1802 and the second implant portion 1804 to displace relative to one another. In some embodiments, an external adjustment device 1810 has a control panel 1812 for input by an operator, a display, 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable power source (e.g., a battery), or may be powered or charged by inductive coupling. The hydraulic pump 1808 may alternatively be replaced by a pneumatic pump.

In some embodiments of the wedge osteotomy devices disclosed herein, the slotted holes may be located on the inner shaft instead of or in addition to the outer housing. The orientation of the implant within the tibia may be opposite of that illustrated in any of the figures. Additionally, any of the embodiments of the non-invasively adjustable wedge osteotomy device may be used for gradual distraction (Ilizarov osteogenesis) or for acute correction of an incorrect angle. And, in some embodiments, alternative, remote adjustment described above may be replaced by manual control of any implanted part, for example manual pressure by the patient or caregiver on a button placed under the skin.

Of course, the foregoing description is of certain features, aspects and advantages of the present invention, to which various changes and modifications can be made without departing from the spirit and scope of the present invention. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different embodiments may be made and still fall within the scope of the invention. Accordingly, it should be understood that various features and aspects of the disclosed embodiments can be combined with or substituted for one another in order to form varying modes of the discussed devices, systems and methods (e.g., by excluding features or steps from certain embodiments, or adding features or steps from one embodiment of a system or method to another embodiment of a system or method).

What is claimed is:

1. A method for modifying a bone of a subject, the method comprising:
   implanting an adjustable implant in the subject;
   passing a first bone anchor through a first portion of the bone and a first bone anchor hole of the adjustable implant;
   passing a second bone anchor through a second portion of the bone and a second bone anchor hole of the adjustable implant; and
   non-invasively causing the adjustable implant to elongate such that a distance between the first bone anchor hole and the second bone anchor hole changes, wherein while the adjustable implant elongates:
   the first bone anchor pivots in at least a first angular direction with respect to the adjustable implant within the first bone anchor hole; and
   the second bone anchor translates in at least a first translation direction with respect to the first bone anchor.

2. The method of claim 1, wherein one or both of the first bone anchor and the second bone anchor is a curved pin.

3. The method of claim 1, wherein implanting the adjustable implant includes placing at least a portion of the adjustable implant inside a longitudinal cavity within the bone.

4. The method of claim 1, further comprising: pivoting the first bone anchor within the first bone anchor hole in a second angular direction opposite the first angular direction.

5. The method of claim 1, further comprising: passing a third bone anchor through a third portion of the bone and a third bone anchor hole.

6. The method of claim 1, wherein non-invasively causing the adjustable implant to elongate includes transcutaneously causing a permanent magnet of the adjustable implant to rotate.

7. The method of claim 1, wherein non-invasively causing the adjustable implant to elongate includes one or more of:
   activating a motor of the adjustable implant;
   inductively activating a motor of the adjustable implant;
   ultrasonically activating a motor of the adjustable implant;
   activating a subcutaneous hydraulic pump; and
   activating a shape-memory driven actuator.

8. The method of claim 1, further comprising:
   creating a wedge osteotomy,
   wherein implanting the first bone anchor includes implanting the first bone anchor above the wedge osteotomy; and
   wherein implanting the second bone anchor includes implanting the second bone anchor below the wedge osteotomy.

9. The method of claim 8, further comprising:
   adding bone graft material within the wedge osteotomy.

10. The method of claim 1, wherein the subject has osteoarthritis of the knee; wherein the bone is a tibia of the subject; and wherein non-invasively causing the adjustable implant to elongate modifies an angle of the tibia.

11. The method of claim 1, wherein non-invasively causing the adjustable implant to elongate occurs while the subject is awake.

12. The method of claim 1, wherein one or both of the first bone anchor and the second bone anchor has a smooth neck, a smooth distal end, and a threaded portion between the smooth neck and smooth distal end; and wherein the method includes threading the threaded portion with the adjustable implant.

13. The method of claim 1, further comprising:
   forming an elongate hole in the bone in a substantially horizontal fashion, wherein the first bone anchor or the second bone anchor is passed through the elongate hole.

14. The method of claim 1, wherein while the adjustable implant elongates: a pivoting region of the adjustable implant pivots about a pivot joint of the adjustable implant.

15. The method of claim 14, wherein the first bone anchor hole is within the pivoting region.

16. The method of claim 1, wherein non-invasively causing the adjustable implant to elongate includes using an external adjustment device to cause the adjustable implant to elongate.

17. A method for treating a tibia of a subject, the method comprising:
   implanting an adjustable implant in the subject, the implant having a raised portion capable of pivoting with respect to the remainder of the adjustable implant;
   passing a first bone anchor through a first portion of the tibia and a first bone anchor hole of the adjustable implant;
   passing a second bone anchor through a second portion of the tibia and a second bone anchor hole of the adjustable implant;
   modifying an angle of the tibia by non-invasively causing the adjustable implant to increase the distance between the first bone anchor hole and the second bone anchor hole; and
   while modifying the angle of the tibia, permitting the first bone anchor to pivot with the raised portion.

18. The method of claim 17, wherein non-invasively causing the adjustable implant to elongate includes one or more of:
   activating a motor of the adjustable implant;
   inductively activating a motor of the adjustable implant;
   ultrasonically activating a motor of the adjustable implant;
   activating a subcutaneous hydraulic pump; and
   activating a shape-memory driven actuator.

* * * * *